United States Patent
Boutell et al.

(10) Patent No.: US 10,858,696 B2
(45) Date of Patent: Dec. 8, 2020

(54) METHODS OF REDUCING DENSITY-DEPENDENT GC BIAS IN AMPLIFICATION

(71) Applicant: ILLUMINA CAMBRIDGE LIMITED, Nr Saffron Walden (GB)

(72) Inventors: Jonathan Mark Boutell, Nr Saffron Walden (GB); Susan Shanahan, Nr Saffron Walden (GB); Roberto Rigatti, Nr Saffron Walden (GB)

(73) Assignee: Illumina Cambridge Limited, Nr. Saffron Walden (GB)

( * ) Notice: Subject to any disclaimer, the term of this patent is extended or adjusted under 35 U.S.C. 154(b) by 0 days.

(21) Appl. No.: 16/511,304

(22) Filed: Jul. 15, 2019

(65) Prior Publication Data

US 2020/0010882 A1 Jan. 9, 2020

Related U.S. Application Data

(62) Division of application No. 15/315,342, filed as application No. PCT/GB2015/051605 on Jun. 2, 2015, now Pat. No. 10,392,655.

(30) Foreign Application Priority Data

Jun. 2, 2014 (GB) .................... 1409777.8

(51) Int. Cl.
*C12Q 1/6844* (2018.01)
*C12Q 1/6806* (2018.01)

(52) U.S. Cl.
CPC ......... *C12Q 1/6846* (2013.01); *C12Q 1/6806* (2013.01)

(58) Field of Classification Search
None
See application file for complete search history.

(56) References Cited

U.S. PATENT DOCUMENTS

| 7,329,860 | B2 | 2/2008 | Feng |
| 7,754,429 | B2 * | 7/2010 | Rigatti ................. C12Q 1/6874 435/6.1 |
| 2005/0100900 | A1 | 5/2005 | Kawashima |
| 2008/0009420 | A1 | 1/2008 | Schroth |
| 2010/0111768 | A1 | 5/2010 | Banerjee |

FOREIGN PATENT DOCUMENTS

| WO | WO1998/44151 | 10/1998 |
| WO | WO1999/46400 | 9/1999 |
| WO | WO2003/048393 | 6/2003 |
| WO | WO 2005/065814 | 7/2005 |
| WO | WO 2007/107710 | 9/2007 |
| WO | WO 2007/123744 | 11/2007 |
| WO | WO2008/002502 | 1/2008 |
| WO | WO 2011/106368 | 9/2011 |
| WO | WO 2012/106072 | 8/2012 |
| WO | WO 2014/043143 | 3/2014 |

OTHER PUBLICATIONS

Jung et al. Journal of Clinical Pathology 2002; 55: 55-57. (Year: 2002).*
Thorp, H.H. Chemistry & Biology 2000; 7: R33-R36. (Year: 2000).*
Saiki et al. (1985) Enzymatic amplification of beta-globin genomic sequences and restriction site analysis for diagnosis of sickle cell anemia, *Science* 230:1350-1354.
Sarkar et, al., Formamide can dramatically improve the specificity of PCR, Nucleic Acids Research 18(24): 7465 (1990).

* cited by examiner

*Primary Examiner* — Angela M. Bertagna
(74) *Attorney, Agent, or Firm* — Knobbe, Martens, Olson & Bear LLP

(57) ABSTRACT

The invention provides methods for amplifying nucleic acids, particularly methods for reducing density-dependent GC bias and for reducing nucleic acid damage in a bridge amplification of a nucleic acid template. The invention also provides methods for evaluating the effect of reagents and/or additives on nucleic acid damage during bridge amplification of nucleic acid template strands. The methods are suited to solid phase amplification, for example, utilizing flow cells.

16 Claims, 27 Drawing Sheets

Lane results summary

| Lane info | | Tile mean +/- SD for lane | | | | | | | |
|---|---|---|---|---|---|---|---|---|---|
| Lane | Lane yield (kbases) | Clusters (raw) | Clusters (PF) | 1st cycle Int (PF) | % intensity after 20 cycles (PF) | % PF clusters | % Align (PF) | Alignment score (PF) | % Error rate (PF) |
| 1 | 94438 | 167783 +/- 9102 | 138067 +/- 32957 | 202 +/- 51 | 106.98 +/- 175.77 | 82.34 +/- 19.53 | 88.74 +/- 21.66 | 116.15 +/- 33.44 | 0.71 +/- 1.25 | 1.5pM no premix
| 2 | 190665 | 405672 +/- 3215 | 278750 +/- 10091 | 143 +/- 12 | 78.18 +/- 4.51 | 68.71 +/- 2.46 | 95.59 +/- 0.18 | 132.15 +/- 0.93 | 0.15 +/- 0.09 | 7.5pM premix
| 3 | 224249 | 447815 +/- 17841 | 311457 +/- 14663 | 192 +/- 16 | 80.63 +/- 2.96 | 69.66 +/- 4.31 | 95.58 +/- 0.00 | 132.47 +/- 0.00 | 0.10 +/- 0.01 | 7.5pM no premix
| 4 | 254968 | 472258 +/- 9014 | 354123 +/- 14414 | 211 +/- 20 | 79.35 +/- 4.02 | 75.00 +/- 2.97 | 95.60 +/- 0.00 | 132.52 +/- 0.29 | 0.09 +/- 0.02 | 7.5pM water protocol
| 5 | 116525 | 171872 +/- 12264 | 161840 +/- 11748 | 274 +/- 16 | 83.96 +/- 5.08 | 94.16 +/- 1.23 | 95.69 +/- 0.21 | 133.39 +/- 0.28 | 0.05 +/- 0.00 | 1.5pM dNTPs protocol
| 6 | 252790 | 475383 +/- 17830 | 351097 +/- 16518 | 236 +/- 15 | 79.62 +/- 4.25 | 73.92 +/- 3.77 | 95.56 +/- 0.00 | 132.43 +/- 0.25 | 0.09 +/- 0.02 | 7.5pM dNTPs protocol
| 7 | 257008 | 470337 +/- 11913 | 356956 +/- 15717 | 206 +/- 22 | 81.19 +/- 3.19 | 75.92 +/- 3.39 | 95.63 +/- 0.13 | 132.71 +/- 0.00 | 0.09 +/- 0.01 | 7.5pM water protocol
| 8 | 256960 | 479137 +/- 16277 | 356889 +/- 13421 | 264 +/- 28 | 81.45 +/- 5.03 | 74.56 +/- 3.54 | 95.57 +/- 0.15 | 132.37 +/- 0.38 | 0.09 +/- 0.02 | 7.5pM dNTPs protocol

| Lane | 1st Solution (120ul) | 2nd Solution (28ul) | 3rd Solution (36ul) |
|---|---|---|---|
| 1 | Wash buffer | Wash buffer | Wash buffer |
| 2 | Formamide | Water | Premix/dNTPs |
| 3 | Formamide | Water | NH4-free premix/dNTPs |
| 4 | Formamide + 1mM Na citrate | Water | NH4-free premix/dNTPs |
| 5 | Formamide + 200uM each nucleotide | Water | NH4-free premix/dNTPs |
| 6 | Formamide + 200uM each nucleotide | Water | Premix/dNTPs |
| 7 | Formamide + 200uM each nucleotide + 3mM MgSO4 | Water | NH4-free premix/dNTPs |
| 8 | Formamide + 1mM EDTA | Water | Premix/dNTPs |

*FIG. 17A*

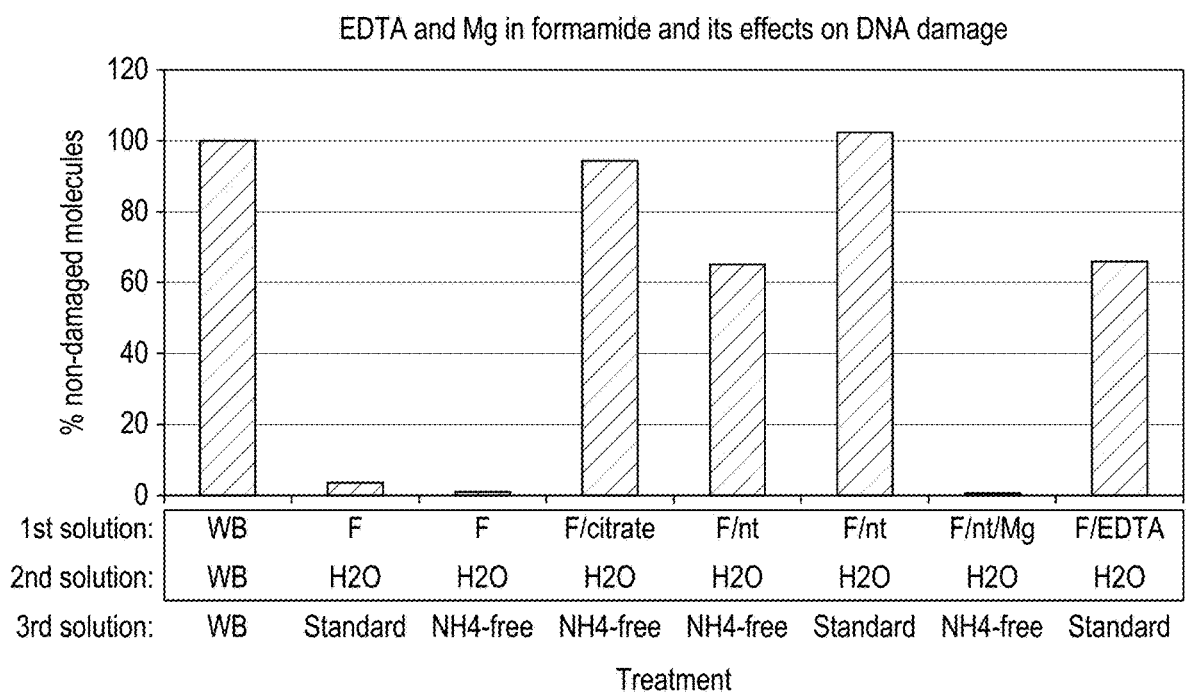

*FIG. 17B*

Lane results summary: Read 1

| Lane info | | Tile mean +/- SD for lane | | | | | | | | |
|---|---|---|---|---|---|---|---|---|---|---|
| Lane | Lane yield (kbases) | Clusters (raw) | Clusters (PF) | 1st cycle Int (PF) | % intensity after 20 cycles (PF) | % PF clusters | % Align (PF) | Alignment score (PF) | % Error rate (PF) | |
| 1 | 61710 | 90908 +/- 2650 | 85709 +/- 2979 | 126 +/- 22 | 80.63 +/- 2.97 | 94.27 +/- 1.34 | 85.45 +/- 0.33 | 81.76 +/- 1.70 | 0.30 +/- 0.42 | 1.0pM 10mM amm |
| 2 | 179644 | 301159 +/- 2379 | 249505 +/- 6820 | 82 +/- 29 | 75.40 +/- 4.90 | 82.84 +/- 1.70 | 85.69 +/- 0.03 | 81.54 +/- 0.66 | 0.29 +/- 0.08 | 5.5pM 10mM amm |
| 3 | 186381 | 308498 +/- 12251 | 258863 +/- 11406 | 94 +/- 36 | 76.78 +/- 3.49 | 83.92 +/- 1.83 | 85.70 +/- 0.22 | 81.45 +/- 1.82 | 0.26 +/- 0.05 | 5.5pM 20mM amm |
| 4 | 179460 | 300064 +/- 4288 | 249250 +/- 6709 | 98 +/- 35 | 78.03 +/- 2.51 | 83.06 +/- 1.48 | 85.72 +/- 0.00 | 82.04 +/- 0.42 | 0.25 +/- 0.04 | 5.5pM 40mM amm |
| 5 | 159158 | 275462 +/- 3248 | 221052 +/- 3295 | 89 +/- 26 | 77.50 +/- 2.04 | 80.24 +/- 1.44 | 85.68 +/- 0.21 | 81.95 +/- 0.18 | 0.25 +/- 0.02 | 5.5pM 80mM amm |
| 6 | 178529 | 295354 +/- 18927 | 247957 +/- 14332 | 82 +/- 27 | 78.75 +/- 2.78 | 84.01 +/- 1.75 | 85.70 +/- 0.00 | 81.92 +/- 0.37 | 0.25 +/- 0.04 | 5.5pM 10mM amm |
| 7 | 176046 | 294977 +/- 9470 | 244509 +/- 10690 | 85 +/- 30 | 79.06 +/- 2.19 | 82.88 +/- 1.96 | 85.71 +/- 0.00 | 82.03 +/- 0.24 | 0.25 +/- 0.03 | 5.5pM 40mM amm |

FIG. 18A

| Lane | 1st Solution (28ul) | 2nd Solution (28ul) | 3rd Solution (36ul) |
|---|---|---|---|
| 1 | Formamide | Bst mix (standard 10mM amm) | Bst mix (standard 10mM amm) |
| 2 | Formamide | Bst mix (standard 10mM amm) | Bst mix (standard 10mM amm) |
| 3 | Formamide + dNTPs | Water + dNTPs | Bst mix (standard 10mM amm) |
| 4 | Formamide + dNTPs | Water + dNTPs | Bst mix (standard 5.0mM amm) |
| 5 | Formamide + dNTPs | Water + dNTPs | Bst mix (standard 2.5mM amm) |
| 6 | Formamide + dNTPs | Water + dNTPs | Bst mix (standard 0.0mM amm) |
| 7 | Formamide + 2M Betaine | Water + dNTPs | Bst mix (standard 10mM amm) |
| 8 | Formamide + 1M Betaine | Water + dNTPs | Bst mix (standard 10mM amm) |

Formamide + 2M Betaine = 60% formamide + 2M Betaine + H2O
Formamide + 1M Betaine = 80% formamide + 1M Betaine + H2O

*FIG. 19A*

Lane results summary

| Lane info | | Tile mean +/- SD for lane | | | | | | | | dNTP method |
|---|---|---|---|---|---|---|---|---|---|---|
| Lane | Lane yield (kbases) | Clusters (raw) | Clusters (PF) | 1st cycle Int (PF) | % intensity after 20 cycles (PF) | % PF clusters | % Align (PF) | Alignment score (PF) | % Error rate (PF) | |
| 1 | 69820 | 101210 +/- 6320 | 96973 +/- 5937 | 290 +/- 10 | 90.74 +/- 1.59 | 95.83 +/- 1.00 | 81.26 +/- 0.19 | 86.23 +/- 0.15 | 0.16 +/- 0.01 | 1.0pM No premix |
| 2 | 267985 | 471469 +/- 16182 | 372201 +/- 10617 | 268 +/- 8 | 86.62 +/- 1.30 | 78.97 +/- 1.39 | 81.42 +/- 0.00 | 85.59 +/- 0.20 | 0.20 +/- 0.01 | 5.5pM No premix |
| 3 | 289332 | 493599 +/- 12105 | 401850 +/- 8629 | 302 +/- 14 | 86.98 +/- 2.37 | 81.43 +/- 1.68 | 81.22 +/- 0.22 | 85.35 +/- 0.00 | 0.18 +/- 0.00 | 5.0pM 10mM amm |
| 4 | 283095 | 483942 +/- 15419 | 393188 +/- 10969 | 269 +/- 6 | 87.13 +/- 1.92 | 81.27 +/- 1.51 | 81.20 +/- 0.17 | 85.31 +/- 0.13 | 0.18 +/- 0.00 | 5.0pM 5.0mM amm |
| 5 | 274016 | 468625 +/- 14523 | 380578 +/- 8580 | 248 +/- 10 | 87.01 +/- 1.82 | 81.24 +/- 1.45 | 81.22 +/- 0.12 | 85.30 +/- 0.12 | 0.18 +/- 0.00 | 5.0pM 2.5mM amm |
| 6 | 254869 | 437317 +/- 20015 | 353985 +/- 15382 | 210 +/- 7 | 86.96 +/- 1.80 | 80.97 +/- 1.51 | 81.21 +/- 0.12 | 85.27 +/- 0.00 | 0.19 +/- 0.00 | 5.0pM 0.0mM amm |
| 7 | 285092 | 492840 +/- 16785 | 395961 +/- 9373 | 278 +/- 12 | 87.40 +/- 1.64 | 80.38 +/- 1.55 | 81.24 +/- 0.00 | 85.35 +/- 0.24 | 0.18 +/- 0.00 | 2M Bet in form |
| 8 | 289208 | 494008 +/- 13950 | 401678 +/- 9425 | 316 +/- 27 | 89.58 +/- 4.30 | 81.33 +/- 1.54 | 81.16 +/- 0.19 | 85.05 +/- 0.70 | 0.22 +/- 0.12 | 1M Bet in form |

FIG. 19B

| | FC61W56AAXX | | | # cycles |
|---|---|---|---|---|
| Lane | 1st Solution (28ul) | 2nd Solution (28ul) | 3rd Solution (36ul) | ⬇ |
| 1 | Formamide | Bst mix (standard 10mM amm) | Bst mix (standard 10mM amm) | 26 |
| 2 | Formamide | Bst mix (standard 10mM amm) | Bst mix (standard 10mM amm) | 26 |
| 3 | Formamide + dNTPs | Water + dNTPs | Bst mix (standard 10mM amm) | 26 |
| 4 | Formamide + dNTPs | Water + dNTPs | Bst mix (standard 0.0mM amm) | 26 |
| 5 | Formamide + 1mM Na Citrane | Water | Bst mix (standard 0.0mM amm) | 26 |
| 6 | Formamide + 1mM Na Citrane | Water + 1mM Na Citrane | Bst mix (standard 0.0mM amm) | 26 |
| 7 | Formamide + dNTPs | Water + dNTPs | Bst mix (standard 0.0mM amm) | 32 |
| 8 | Formamide + 1mM Na Citrane | Water | Bst mix (standard 0.0mM amm) | 32 |

*FIG. 20A*

Lane results summary: Read 1

| Lane info | | Tile mean +/- SD for lane | | | | | | | | |
|---|---|---|---|---|---|---|---|---|---|---|
| Lane | Lane yield (Mbases) | Clusters (raw) | Clusters (PF) | 1st cycle Int (PF) | % intensity after 20 cycles (PF) | % PF clusters | % Align (PF) | Alignment score (PF) | % Error rate (PF) | |
| 1 | 60 | 82426 +/- 9349 | 75623 +/- 2408 | 292 +/- 34 | 92.30 +/- 17.83 | 92.55 +/- 7.63 | 85.42 +/- 0.87 | 80.79 +/- 4.30 | 0.41 +/- 0.58 | 0.7pM No premix |
| 2 | 272 | 399931 +/- 12424 | 343252 +/- 10154 | 269 +/- 9 | 86.68 +/- 2.41 | 85.84 +/- 1.53 | 85.67 +/- 0.57 | 81.17 +/- 2.17 | 0.24 +/- 0.06 | 5.0pM No premix |
| 3 | 296 | 422726 +/- 7121 | 373315 +/- 5079 | 307 +/- 5 | 85.60 +/- 2.13 | 88.32 +/- 0.63 | 85.74 +/- 0.11 | 81.82 +/- 0.14 | 0.21 +/- 0.00 | 5.0pM dNTPs 10mM |
| 4 | 267 | 380804 +/- 8469 | 336566 +/- 7047 | 224 +/- 5 | 86.79 +/- 2.19 | 88.39 +/- 0.38 | 85.71 +/- 0.00 | 81.78 +/- 0.00 | 0.22 +/- 0.01 | 5.0pM dNTPs 0.0mM ⎫ |
| 5 | 283 | 403808 +/- 8493 | 347415 +/- 5896 | 232 +/- 5 | 87.47 +/- 2.00 | 88.52 +/- 0.62 | 85.71 +/- 0.13 | 81.80 +/- 0.00 | 0.21 +/- 0.00 | 5.0pM Citrate in form ⎬ NH4-free |
| 6 | 258 | 370978 +/- 22164 | 326232 +/- 16963 | 214 +/- 13 | 87.25 +/- 2.49 | 87.98 +/- 0.73 | 85.69 +/- 0.20 | 81.74 +/- 0.21 | 0.22 +/- 0.00 | 5.0pM Citrate in form and H2O |
| 7 | 294 | 415625 +/- 19497 | 371202 +/- 15753 | 261 +/- 11 | 87.36 +/- 1.82 | 89.33 +/- 0.61 | 85.66 +/- 0.18 | 81.67 +/- 0.25 | 0.22 +/- 0.00 | 5.0pM dNTPs 10mM, top-up ⎭ |
| 8 | 293 | 420844 +/- 8715 | 369664 +/- 6938 | 308 +/- 52 | 86.88 +/- 2.11 | 87.84 +/- 0.69 | 85.65 +/- 0.10 | 81.50 +/- 0.24 | 0.23 +/- 0.05 | 5.0pM Citrate in form, top-up |

FIG. 20B

| Lane | 1st Solution (28ul) | 2nd Solution (28ul) | 3rd Solution (36ul) |
|---|---|---|---|
| 1 | Formamide | Pre-mix | Bst mix (standard 10mM amm) |
| 2 | Formamide | Pre-mix | Bst mix (standard 10mM amm) |
| 3 | Formamide + 1mM Na Citrane | Water | Bst mix (NH4-free) |
| 4 | Formamide + 5mM Na Citrane | Water | Bst mix (NH4-free) |
| 5 | Formamide + 1mM Na Citrane | Water | Bst mix (NH4-free) |
| 6 | Formamide + 10mM Na Citrane | Water | Bst mix (NH4-free) |
| 7 | Formamide + 3.2M Betaine | Water | Bst mix (NH4-free) |
| 8 | Formamide + 3.2M Betaine | Water | Bst mix (NH4-free) |

*FIG. 21A*

Lane results summary

| Lane | Lane yield (Mbases) | Clusters (raw) | Clusters (PF) | 1st cycle Int (PF) | % intensity after 20 cycles (PF) | % PF clusters | % Align (PF) | Alignment score (PF) | % Error rate (PF) | |
|---|---|---|---|---|---|---|---|---|---|---|
| | | Tile mean +/- SD for lane | | | | | | | | |
| 1 | 81887 | 124672 +/- 9803 | 113732 +/- 9485 | 68 +/- 3 | 70.84 +/- 2.03 | 91.20 +/- 0.55 | 80.50 +/- 0.30 | 78.95 +/- 0.92 | 0.38 +/- 0.09 | 0.7pM standard amp (35 cycles) |
| 2 | 252389 | 462767 +/- 17904 | 350541 +/- 4040 | 85 +/- 6 | 68.94 +/- 2.29 | 75.84 +/- 2.51 | 81.04 +/- 0.19 | 79.88 +/- 0.70 | 0.35 +/- 0.05 | 5.0pM standard amp (35 cycles) |
| 3 | 271010 | 485091 +/- 20033 | 376403 +/- 7387 | 89 +/- 3 | 70.40 +/- 1.64 | 77.69 +/- 2.79 | 80.81 +/- 0.20 | 79.72 +/- 0.47 | 0.31 +/- 0.03 | 5.0pM 1mM Na Citrate (32 cycles) |
| 4 | 275411 | 483346 +/- 19966 | 382516 +/- 6915 | 88 +/- 3 | 71.56 +/- 1.70 | 79.23 +/- 2.67 | 80.90 +/- 0.21 | 78.85 +/- 0.45 | 0.29 +/- 0.02 | 5.0pM 5mM Na Citrate (32 cycles) |
| 5 | 82983 | 123128 +/- 11659 | 115255 +/- 11256 | 69 +/- 4 | 70.08 +/- 2.58 | 93.58 +/- 0.45 | 80.67 +/- 0.24 | 79.56 +/- 0.89 | 0.31 +/- 0.08 | 0.7pM 1mM Na Citrate (32 cycles) |
| 6 | 281421 | 484869 +/- 16717 | 390862 +/- 5813 | 80 +/- 6 | 71.59 +/- 2.15 | 80.69 +/- 2.55 | 80.85 +/- 0.30 | 79.95 +/- 0.64 | 0.28 +/- 0.04 | 5.0pM 10mM Na Citrate (32 cycles) |
| 7 | 272759 | 487812 +/- 15356 | 378832 +/- 6871 | 83 +/- 5 | 71.53 +/- 2.30 | 77.75 +/- 3.32 | 80.94 +/- 0.07 | 80.06 +/- 0.55 | 0.28 +/- 0.04 | 5.0pM 3.2M Betaine (32 cycles) |
| 8 | 272522 | 484751 +/- 15993 | 378503 +/- 9792 | 89 +/- 8 | 72.99 +/- 2.35 | 78.16 +/- 3.07 | 80.95 +/- 0.12 | 80.25 +/- 0.53 | 0.26 +/- 0.04 | 5.0pM 3.2M Betaine (32 cycles) |

FIG. 21B

METHODS OF REDUCING DENSITY-DEPENDENT GC BIAS IN AMPLIFICATION

CROSS-REFERENCE TO RELATED APPLICATIONS

This application is a division of U.S. Ser. No. 15/315,342 filed on Nov. 30, 2016 now U.S. Pat. No. 10,392,655 which issued on Aug. 27, 2019 which is the U.S. National Phase of Int. App. No. PCT/GB2015/051605 filed Jun. 2, 2015 which published in English as WO 2015/185916 on Dec. 10, 2015 which claims the benefit of priority to GB 1409777.8 filed Jun. 2, 2014 which are each incorporated by reference in its entirety.

FIELD OF THE INVENTION

The invention relates to methods of amplification of polynucleotide sequences and in particular relates to methods for amplification of polynucleotide sequences to minimize sequence specific biases. The methods according to the present invention are suited to solid phase amplification, for example, utilizing flow cells.

BACKGROUND

The Polymerase Chain Reaction or PCR (Saiki et al. (1985) Science 230:1350) has become a standard molecular biology technique which allows for amplification of nucleic acid molecules. This in-vitro method is a powerful tool both for the detection and analysis of small quantities of nucleic acids and other recombinant nucleic acid technologies.

Briefly, PCR typically utilizes a number of components: a target nucleic acid molecule, a molar excess of a forward and reverse primer which bind to the target nucleic acid molecule, deoxyribonucleoside triphosphates (dATP, dTTP, dCTP and dGTP) and a polymerase enzyme.

The PCR reaction is a DNA synthesis reaction that depends on the extension of the forward and reverse primers annealed to opposite strands of a dsDNA template that has been denatured (melted apart) at high temperature (90° C. to 100° C.). Using repeated melting, annealing and extension steps usually carried out at differing temperatures, copies of the original template DNA are generated.

Amplification of template sequences by PCR typically draws on knowledge of the template sequence to be amplified such that primers can be specifically annealed to the template. The use of multiple different primer pairs to simultaneously amplify different regions of the sample is known as multiplex PCR, and suffers from numerous limitations, including high levels of primer dimerization, and the loss of sample representation due to the different amplification efficiencies of the different regions.

For the multiplex analysis of large numbers of target fragments, it is often desirable to perform a simultaneous amplification reaction for all the targets in the mixture, using a single pair of primers for all the targets. In certain embodiments, one or more of the primers may be immobilized on a solid support. Such universal amplification reactions are described more fully in U.S. Patent App. Pub. No. 2005/0100900, the entire disclosure of which is incorporated herein by reference. Isothermal amplification methods for nucleic acid amplification are described in U.S. Patent App. Pub. No. 2008/0009420, the entire disclosure of which is incorporated herein by reference. The methods involved may rely on the attachment of universal adapter regions, which allows amplification of all nucleic acid templates from a single pair of primers.

The universal amplification reaction can still suffer from limitations in amplification efficiency related to the sequences of the templates. One manifestation of this limitation is that the mass or size of different nucleic acid clusters varies in a sequence dependent manner. For example, the AT rich clusters can gain more mass or become larger than the GC rich clusters. As a result, analysis of different clusters may lead to bias. For example, in applications where clusters are analyzed using sequencing by synthesis techniques, the GC rich clusters may appear smaller or dimmer such that the clusters are detected less efficiently. This results in lower representation of sequence data for GC rich clusters than the brighter (more intense) and larger AT rich clusters. This can result in lower representation and less accurate sequence determination for the GC rich templates, an effect which may be termed GC bias.

The presence of sequence specific bias during amplification gives rise to difficulties determining the sequence of certain regions of the genome, for example GC rich regions such as CpG islands in promoter regions. The resulting lack of sequence representation in the data from clusters of different GC composition translates into data analysis problems such as increases in the number of gaps in the analyzed sequence; a yield of shorter contigs, giving rise to a lower quality de novo assembly; identifying SNPs less accurately in GC rich regions due to low coverage of these regions; and a need for increased coverage to sequence a genome, thereby increasing the cost of sequencing genomes.

The problem of bias may be more acute when the density of clusters on the solid support is high. In certain situations, as the clusters grow, the amplification primers on the solid support are all extended, and hence adjacent clusters cannot expand over the top of each other due to the lack of available amplification primers. The over-amplification of AT rich sequences causes rapid consumption of the primers on the surface, and hence reduces the ability of the GC rich sequences to amplify.

In particular embodiments, the methods and compositions presented herein are aimed at reducing density-dependent GC bias in isothermal acid amplification reactions.

One aspect of the invention provides a method for reducing density-dependent GC bias and/or nucleic acid damage in bridge amplification of a double stranded nucleic acid template on a surface comprising:
  a. denaturing the nucleic acid template with a first solution to produce single stranded nucleic acid template strands;
  b. optionally replacing the first solution with a second solution;
  c. annealing the single stranded nucleic acid template strands to oligonucleotide primers bound to the surface; and
  d. replacing the first or second solution with a solution comprising a polymerase, whereby the oligonucleotide primers bound to the surface are fully extended;
  wherein at least one of the solutions comprises at least one additive and density-dependent GC bias and/or nucleic acid damage in the isothermal amplification of the double stranded nucleic acid template is reduced.

One type of primer may be on the surface and the other primer in solution.

Preferably, at least one of the first and second solutions comprises at least one additive.

In one embodiment, only the solution comprising a polymerase comprises an additive, such as a high concentration of betaine.

The bridge amplification may be a substantially isothermal bridge amplification.

The nucleic acid may comprise DNA or RNA.

Optionally, the surface is a flow cell surface.

In one embodiment, the surface may comprise a bead.

Replacing the first or second solution may comprise mixing solutions and/or gradually replacing a solution via a continuous gradient.

Preferably, a cluster of identical nucleic acid strands is generated.

In a preferred embodiment, the first solution comprises formamide.

The additive may comprise a chelating agent.

The additive may comprise a mixture of different dNTPs and/or rNTPs.

The additive may comprise a single type of dNTP and/or a single type of rNTP.

The additive may comprise at least one citrate.

The at least one citrate may be selected from: monosodium citrate, disodium citrate, trisodium citrate, and potassium citrate.

The additive may comprise EDTA.

The additive may comprise betaine.

The additive may comprise DMSO.

Preferably, the second solution comprises a low ionic strength solution.

In one embodiment, the second solution comprises water.

Preferably, the second solution comprises less than about 100 mM of salt.

Preferably, the second solution comprises less than about 80 mM of salt; more preferably less than about 40 mM of salt; even more preferably less than about 20 mM of salt, more preferably less than about 10 mM of salt. Even more preferably, the second solution comprises less than about 5 mM of salt.

In one embodiment, the second solution is substantially free from any salt.

In one embodiment, the second solution comprises a pre-mix solution.

The pre-mix solution may comprise one or more salts and/or buffers.

The pre-mix solution may comprise DMSO and/or betaine.

In one embodiment, the second solution does not comprise an additive.

Preferably, the solution comprising the polymerase comprises a mixture of different dNTPs or rNTPs.

In an embodiment in which the nucleic acid comprises DNA, the solution comprising the polymerase comprises dNTPs.

In an embodiment in which the nucleic acid comprises RNA, the solution comprising the polymerase comprises rNTPs.

In an embodiment in which the nucleic acid comprises DNA, the polymerase preferably comprises a DNA polymerase.

Optionally, the DNA polymerase comprises a Bst polymerase.

In an embodiment in which the nucleic acid comprises RNA, the polymerase preferably comprises an RNA polymerase.

In an embodiment in which the nucleic acid comprises RNA, the solution comprising the polymerase preferably comprises a mixture of rNTPs.

Optionally, the solution comprising the polymerase comprises at least one additive selected from one or more of the following: EDTA, a mixture of dNTPs, a single type of dNTP, a mixture of rNTPs, a single type of rNTP, a citrate, a citrate salt, monosodium citrate, disodium citrate, trisodium citrate, potassium citrate, betaine, DMSO.

In one embodiment additive comprises a high concentration of betaine.

Preferably, the solution comprising the polymerase does not comprise ammonium sulphate.

Preferably, the solution comprising the polymerase comprises less than about 100 mM of any salt.

Preferably, the solution comprising the polymerase comprises less than about 80 mM of salt; more preferably less than about 40 mM of salt; even more preferably less than about 20 mM of salt, more preferably less than about 10 mM of salt. Even more preferably, the solution comprising the polymerase comprises less than about 5 mM of salt.

In one embodiment, the solution comprising the polymerase is substantially free from any salt.

In one embodiment, the solution comprising the polymerase comprises one or more salts and/or buffers.

In one embodiment, the solution comprising the polymerase comprises DMSO and/or betaine.

Optionally, the additive may comprise a mixture of ddNTPs or a single type of ddNTP.

Steps (a) to (d) of the method are preferably performed two or more times.

The steps may be performed about 35 times, or less.

In one embodiment, the steps are performed more than 35 times. In one embodiment, the steps are performed around 50 times.

The steps may be performed at about 60° C., or less.

The steps may be performed at about 50° C. or less. The steps may be performed at about 40° C. or less. The steps may be performed at about 30° C. or less.

The steps may be performed while the temperature is being cycled between two or more different temperatures.

Another aspect of the invention provides a method for evaluating damage of nucleic acid strands by a reagent and/or additive comprising;
  attaching the nucleic acid strands to a surface;
  introducing the reagent and/or additive to the nucleic acid strands attached to the surface;
  visualising the nucleic acid strands to detect damage thereof by the reagent and/or additive.

The amount of damage may be quantified.

Preferably, the amount of damage is evaluated by detecting the number of undamaged molecules and comparing the number to the number of undamaged molecules obtained in a control method.

The control method lacks the introduction of the reagent and/or additive.

The step of attaching the nucleic acid strands to a surface optionally comprises seeding the surface with the nucleic acid strands whereby single stranded nucleic acid strands anneal to oligonucleotide primers bound to the surface.

The oligonucleotide primers may be extended using a polymerase.

Optionally, the method includes the step of denaturing single stranded nucleic acid strands, whereby single stranded nucleic acid molecules covalently bound to the oligonucleotide primers bound to the flow cell surface are produced.

Optionally, the method includes the step of performing a mock amplification method on the single stranded nucleic acid molecules covalently bound to the oligonucleotide primers bound to the flow cell surface The method may comprise cycling the reagent and/or additive, pumping the reagent and/or additive substantially continuously to the nucleic acid strands In another embodiment, the step of introducing the reagent and/or additive comprises substantially static incubation with the nucleic acid strands.

Optionally, the method includes the step of performing an amplification method on the single stranded nucleic acid molecules covalently bound to the oligonucleotide primers and visualizing clusters of identical nucleic acid strands.

Preferably, the amplification is carried out after the nucleic acid damaging treatment.

The amplification method may comprise bridge amplification.

Clusters of identical nucleic acid strands may be stained with a binding dye and imaged.

Advantageously, the number of clusters of identical nucleic acid strands is inversely proportional to the amount of damage.

In one embodiment, the step of extending the oligonucleotide primers using a polymerase may be performed after the step of performing the mock isothermal amplification.

The reagent may comprise a cluster amplification reagent.

The reagent may comprise a damaging agent of physical or chemical or physical nature.

The additive may comprise one or more of: a chelating agent, EDTA, a mixture of dNTPs, a single type of dNTP, a citrate, a citrate salt, monosodium citrate, disodium citrate, trisodium citrate, potassium citrate, betaine, DMSO.

Optionally, the method is for evaluating the effect of cluster amplification reagents and/or additives on nucleic acid damage.

The method may be for evaluating the effect of chemical or physical agents, on nucleic acid damage.

The nucleic acid may comprise DNA or RNA.

In one embodiment the nucleic acid comprises single stranded DNA.

In one embodiment, the nucleic acid comprises double stranded DNA.

The method may include a preliminary step of denaturing double stranded DNA to provide single stranded template strands.

Optionally, the amplification method comprises substantially isothermal bridge amplification.

The mock amplification method may comprise;
i. adding a first solution comprising a first additive to the single stranded nucleic acid molecules covalently bound to the oligonucleotide primers bound to the flow cell surface;
ii. replacing the first solution with a second solution comprising a second additive; and
iii. replacing the second solution with a third solution that does not comprise a polymerase.
wherein density-dependent GC bias and/or nucleic acid damage in the isothermal amplification of the double stranded nucleic acid template is reduced.

Optionally, the method is for evaluating nucleic acid damage during bridge amplification.

The mock amplification may be a substantially isothermal mock amplification.

In one embodiment, the step of performing an amplification method comprises
a. denaturing a nucleic acid template with a first solution to produce single stranded nucleic acid template strands;
b. optionally replacing the first solution with a second solution;
c. annealing the single stranded nucleic acid template strands to oligonucleotide primers bound to the surface; and
d. replacing the first or second solution with a solution comprising a polymerase, whereby the oligonucleotide primers bound to the surface are fully extended;
wherein at least one of the first and second solutions comprises at least one additive and density-dependent GC bias and/or nucleic acid damage in the isothermal amplification of the double stranded nucleic acid template is reduced.

The bridge amplification may be a substantially isothermal bridge amplification.

The nucleic acid may comprise DNA or RNA.

Optionally, the surface is a flow cell surface.

In one embodiment, the surface may comprise a bead.

Replacing the first or second solution may comprise mixing solutions and/or gradually replacing a solution via a continuous gradient.

Preferably, a cluster of identical nucleic acid strands is generated.

In a preferred embodiment, the first solution comprises formamide.

The additive may comprise a chelating agent.

The additive may comprise a mixture of different dNTPs and/or rNTPs.

The additive may comprise a single type of dNTP and/or a single type of rNTP.

The additive may comprise at least one citrate.

The at least one citrate may be selected from: monosodium citrate, disodium citrate, trisodium citrate, and potassium citrate.

The additive may comprise EDTA.

The additive may comprise betaine.

The additive may comprise DMSO.

Preferably, the second solution comprises a low ionic strength solution.

In one embodiment, the second solution comprises water.

Preferably, the second solution comprises less than about 100 mM of salt.

Preferably, the second solution comprises less than about 80 mM of salt; more preferably less than about 40 mM of salt; even more preferably less than about 20 mM of salt, more preferably less than about 10 mM of salt. Even more preferably, the second solution comprises less than about 5 mM of salt.

In one embodiment, the second solution is substantially free from any salt.

In one embodiment, the second solution comprises a pre-mix solution.

The pre-mix solution may comprise one or more salts and/or buffers.

The pre-mix solution may comprise DMSO and/or betaine.

In one embodiment, the second solution does not comprise an additive.

Preferably, the solution comprising the polymerase comprises a mixture of different dNTPs or rNTPs.

In an embodiment in which the nucleic acid comprises DNA, the solution comprising the polymerase comprises dNTPs.

In an embodiment in which the nucleic acid comprises RNA, the solution comprising the polymerase comprises rNTPs.

In an embodiment in which the nucleic acid comprises DNA, the polymerase preferably comprises a DNA polymerase.

Optionally, the DNA polymerase comprises a Bst polymerase.

In an embodiment in which the nucleic acid comprises RNA, the polymerase preferably comprises an RNA polymerase.

In an embodiment in which the nucleic acid comprises RNA, the solution comprising the polymerase preferably comprises a mixture of rNTPs.

Optionally, the solution comprising the polymerase comprises at least one additive selected from one or more of the following: EDTA, a mixture of dNTPs, a single type of dNTP, a mixture of rNTPs, a single type of rNTP, a citrate, a citrate salt, monosodium citrate, disodium citrate, trisodium citrate, potassium citrate, betaine, DMSO.

In one embodiment additive comprises a high concentration of betaine.

Preferably, the solution comprising the polymerase does not comprise ammonium sulphate.

Preferably, the solution comprising the polymerase comprises less than about 100 mM of any salt.

Preferably, the solution comprising the polymerase comprises less than about 80 mM of salt; more preferably less than about 40 mM of salt; even more preferably less than about 20 mM of salt, more preferably less than about 10 mM of salt. Even more preferably, the solution comprising the polymerase comprises less than about 5 mM of salt.

In one embodiment, the solution comprising the polymerase is substantially free from any salt.

In one embodiment, the solution comprising the polymerase comprises one or more salts and/or buffers.

In one embodiment, the solution comprising the polymerase comprises DMSO and/or betaine.

Optionally, the additive may comprise a mixture of ddNTPs or a single type of ddNTP.

Steps of the method are preferably performed two or more times.

The steps may be performed about 35 times, or less. In one embodiment, the steps are performed more than 35 time. In one embodiment, the steps are performed around 50 times.

The steps may be performed at about 60° C., or less. The steps may be performed at about 50° C. or less. The steps may be performed at about 40° C. or less. The steps may be performed at about 30° C. or less.

In one embodiment, the first solution comprises formamide and at least one additive, the second solution comprises water and no additive, and the solution comprising the polymerase comprises no additive.

Another aspect of the invention provides a system for bridge amplification comprising apparatus having at least one inlet, and at least one outlet; and means for reducing density-dependent GC bias and/or nucleic acid damage in a bridge amplification of a double stranded nucleic acid template on a surface.

The system preferably comprises control means for coordinating the steps of the method.

The apparatus may comprise means for immobilizing primers on a surface.

Optionally, the apparatus comprises a flow cell and solutions are applied through the inlet and removed through the outlet by a process of solution exchange.

Optionally, the system comprises detection means for detecting a fluorescent signal.

Yet another aspect of the invention provides a system for evaluating nucleic acid damage comprising apparatus having at least one inlet, and at least one outlet; and means for evaluating nucleic acid damage of nucleic acid strands on a surface.

Preferably, the surface comprises a flow cell surface.

In one embodiment the system is for evaluating nucleic acid damage during bridge amplification.

Yet another aspect of the invention provides a kit for reducing density-dependent GC bias and/or nucleic acid damage in a bridge amplification of a double stranded nucleic acid template on a surface comprising;

a first solution for producing single stranded nucleic acid template strands; at least one additive; and a polymerase.

Optionally the bridge amplification comprises substantially isothermal bridge amplification.

Preferably the at least one additive comprises: a chelating agent, EDTA, a mixture of dNTPs, a single type of dNTP, a mixture of rNTPs, a single type of rNTP, a citrate, a citrate salt, monosodium citrate, disodium citrate, trisodium citrate, potassium citrate, betaine and/or DMSO.

The first solution may comprise formamide.

Optionally, the kit further comprises a second solution comprising a pre-mix and/or water.

Yet another aspect of the invention provides a kit for evaluating nucleic acid damage of nucleic acid template strands on a surface comprising at least one reagent and/or additive and means for visualising the nucleic acid strands.

Means for visualising the nucleic acid strands may comprise a dye.

Optionally, the kit or system is for evaluating the effect of cluster amplification reagents on nucleic acid damage.

The kit may comprise primers and/or instructions for performing the method.

BRIEF DESCRIPTION

A method for reducing density-dependent GC bias in an isothermal bridge amplification of a double stranded DNA (dsDNA) template on a flow cell surface is provided, comprising: a) denaturing the dsDNA template with a first solution comprising a first additive to produce single stranded DNA (ssDNA) template strands; b) replacing the first solution with a second solution which may comprise a second additive, whereby the ssDNA template strands anneal to oligonucleotide primers bound to the flow cell surface; and c) replacing the second solution with a third solution comprising a DNA polymerase, whereby the oligonucleotide primers bound to the flow cell surface are fully extended; wherein density-dependent GC bias in the isothermal amplification of the dsDNA template is reduced. In one embodiment, a cluster of identical DNA strands is generated. In another embodiment, the first solution comprises formamide. In one embodiment, the first solution further comprises EDTA. In one embodiment, the first solution comprises formamide together with a high concentration of betaine. In some embodiments, the first additive is a mixture of different dNTPs or is a single type of dNTP. In a further embodiment, the first additive is trisodium citrate. In still further embodiments, the second additive is a mixture of different dNTPs. In some embodiments, the second solution further comprises a pre-mix solution, particularly wherein the pre-mix solution comprises one or more salts and one or more buffers, more particularly wherein the pre-mix solution comprises DMSO and/or Betaine. In another embodiment, the second solution comprises water.

In yet another embodiment, the DNA polymerase is a Bst DNA polymerase. In further embodiments, the third solution further comprises a mixture of different dNTPs. In still further embodiments, the third solution comprises one or more salts and one or more buffers, particularly wherein the pre-mix solution comprises DMSO and/or Betaine. In another embodiment, the third solution does not comprise ammonium sulfate. In additional embodiments, steps (a) to (c) are performed two or more times, particularly wherein steps (a) to (c) are performed about 35 times, and more particularly wherein steps (a) to (c) are performed at about 60° C.

In some embodiments, the temperature at which steps (a) to (c) are performed may be adjusted according to the optimum temperature for the type of DNA polymerase used.

A method for evaluating the effect of cluster amplification reagents and/or additives on DNA damage during isothermal bridge amplification of ssDNA template strands on a flow cell surface is also provided, comprising: a) seeding the flow cell surface with the ssDNA template strands, whereby the ssDNA template strands anneal to oligonucleotide primers bound to the flow cell surface; b) extending the oligonucleotide primers using a DNA polymerase; c) denaturing the dsDNA template strands, whereby ssDNA molecules covalently bound to the oligonucleotide primers bound to the flow cell surface are produced; d) performing a mock isothermal amplification method on the ssDNA molecules covalently bound to the oligonucleotide primers bound to the flow cell surface, comprising cycling cluster amplification reagents and/or additives; e) performing an isothermal amplification method on the ssDNA molecules covalently bound to the oligonucleotide primers bound to the flow cell surface; and f) visualizing clusters of identical DNA strands, wherein clusters of identical DNA strands are stained with a DNA binding dye and imaged; wherein the number of clusters of identical DNA strands is inversely proportional to the amount of DNA damage caused by the cluster amplification reagents and/or additives. In one embodiment, the mock isothermal amplification method comprises: i) adding a first solution comprising a first additive to the ssDNA molecules covalently bound to the oligonucleotide primers bound to the flow cell surface; ii) replacing the first solution with a second solution comprising a second additive; and iii) replacing the second solution with a third solution that does not comprise a DNA polymerase. In an alternative embodiment, step (d) may be replaced with an alternative step (d) of pumping amplification reagents and/or additives substantially continuously to the ssDNA molecules covalently bound to the oligonucleotide primers bound to the flow cell surface.

In one embodiment, the first solution, second solution and/or third solutions used in step (d) do not comprise additives.

In another embodiment, the isothermal amplification method comprises: i) adding a first solution comprising a first additive to the ssDNA molecules covalently bound to the oligonucleotide primers bound to the flow cell surface; ii) replacing the first solution with a second solution comprising a second additive; and iii) replacing the second solution with a third solution comprising a DNA polymerase.

In one embodiment, the first solution, second solution and/or third solutions used in the isothermal amplification step (e) do not comprise additives.

In some embodiments, the first solution comprises formamide. The first additive may comprise one or more of the following: a chelating agent, EDTA, a mixture of dNTPs, a single type of dNTP, a mixture of rNTPs, a single type of rNTP, a citrate, a citrate salt, sodium citrate, disodium citrate, trisodium citrate, potassium citrate, betaine, DMSO.

In one embodiment, the first additive comprises EDTA. In some embodiments, the first additive is a mixture of different dNTPs or the first additive is a single type of dNTP. In a further embodiment, the first additive is trisodium citrate. In still further embodiments, the second additive is a mixture of different dNTPs. In some embodiments, the second solution comprises a pre-mix solution, particularly wherein the pre-mix solution comprises one or more salts and one or more buffers, more particularly wherein the pre-mix solution comprises DMSO and/or Betaine. In another embodiment, the second solution comprises water.

The second additive may comprise one or more of the following: a chelating agent, EDTA, a mixture of dNTPs, a single type of dNTP, a citrate, a citrate salt, monosodium citrate, disodium citrate, trisodium citrate, potassium citrate, betaine, DMSO.

In yet another embodiment, the DNA polymerase is a Bst DNA polymerase. In further embodiments, the third solution further comprises a mixture of different dNTPs. In still further embodiments, the third solution comprises one or more salts and one or more buffers, particularly wherein the pre-mix solution comprises DMSO and/or Betaine. In another embodiment, the third solution does not comprise ammonium sulphate or other salt. In additional embodiments, steps (a) to (d) are performed two or more times, particularly wherein steps (a) to (d) are performed about 26 times, more particularly wherein steps (a) to (d) are performed about 35 times or lower, and even more particularly wherein steps (a) to (d) are performed at about 60° C.

In some embodiments, the temperature at which steps (a) to (d) are performed may be adjusted according to the optimum temperature for the type of DNA polymerase used in the amplification process.

A method for reducing DNA damage in an isothermal bridge amplification of a dsDNA template on a flow cell surface is also provided, comprising: a) denaturing the dsDNA template with a first solution comprising formamide to produce single stranded DNA (ssDNA) template strands; b) replacing the first solution with a second solution comprising dNTPs, whereby the ssDNA template strands anneal to oligonucleotide primers bound to the flow cell surface; and c) replacing the second solution with a third solution comprising a DNA polymerase, whereby the oligonucleotide primers bound to the flow cell surface are fully extended; wherein DNA damage in the isothermal amplification of the dsDNA template is reduced.

BRIEF DESCRIPTION OF THE DRAWINGS

FIG. 11 shows a data table of sequencing metrics for a sequencing run evaluating the "dNTPs method" and the "water method".

FIG. 17A and FIG. 17B each relate to the effect of the presence in formamide of the chelating molecule EDTA and of the ion magnesium on DNA damage (FC6254LAAXX, exp 12473). FIG. 17A depicts an experiment design. CT180 was seeded at 1 pM. 1st strand extension was done using Taq DNA polymerase followed by NaOH denaturation. Single molecules were then treated with 26 cycles of "mock isothermal amplification (28 µl formamide, 28 µl H$_2$O, 36 µl premix with dNTPs except for lane 1 which was treated with wash buffer for the entire duration. The pre-mix was either standard containing 10 mM ammonium sulfate or a pre-mix that was ammonium sulphate-free. EDTA (0.5M, pH 8.0) was added to formamide to a final concentration of 1 mM. dNTPs were added to formamide to a final concentration of 200 µM of each nucleotide (800 µM total concentration). In lane 7, Mg sulphate was added to a final concentration of 3 mM to the dNTPs containing formamide solution. After bridge amplification, clusters were then stained with sybr green and three tiles per lane were imaged using a microscope and a camera. Clusters numbers were determined using a software called Firecrest. FIG. 17B is a graph in which cluster numbers are plotted as a percentage of lane 1 (wash buffer treated control lane).

FIG. 18A, FIG. 18B and FIG. 18C depict an effect of increasing the concentration of ammonium sulphate in the Bst mix on density-dependent GC bias. FIG. 18A depicts a run summary; FIG. 18B and FIG. 18C depict GC bias curves from experiment 100526_EAS20_0170_FC61LRUAAXX. CT3576 (standard human library, 300 bp insert average size) was seeded at either low density (1 pM) or high density (5.5 pM). After standard first strand extension with Phusion, cluster were amplified with 26 cycles of isothermal amplification using 28 µl of formamide followed by 28 µl of water and 36 µl of Bst mix with different concentrations of ammonium sulphate (ranging between the standard 10 mM concentration and up to 80 mM). The bias curves in FIG. 18C were obtained from the curves in FIG. 18B by dividing each curve by the low density lane (lane 1) curve as a way of focusing exclusively on the density-dependent component of the GC bias created during cluster amplification.

FIG. 19A, FIG. 19B, and FIG. 19C depict combined effect of dNTPs in formamide and lower ammonium sulphate concentrations in Bst mix on density-dependent GC bias. The experiment design is shown in FIG. 19A. After seeding a standard human library (CT3576) at high and low density and 1st strand extension with Phusion, clusters were amplified using 26 cycles of isothermal amplification with the conditions shown in the table. After read 1 preparation the flowcell was sequenced with a GAIIx instrument. This particular run was a paired end experiment using the 95G chemistry sequencing 36 bases in each read. Analysis was carried out with pipeline 1.6. FIG. 19B shows the summary for read 1 whereas in FIG. 19C are shown the normalised GC bias curves (obtained by dividing the original GC bias curves by the curve at low density (lane 1).

FIG. 20A, FIG. 20B, FIG. 20C and FIG. 20D depict combining sodium citrate with ammonium-free Bst mix and top-up cycles. The experiment design is shown in FIG. 20A. After seeding of the standard human library (CT3576) at high and low density and 1st strand extension with Phusion, clusters were amplified using 26 or 32 cycles of isothermal amplification with the conditions shown in the table. After read 1 preparation the flowcell was sequenced with a GAIIx instrument. This particular experiment was a paired end run using the 95G chemistry sequencing 36 bases in each read. Analysis was carried out with pipeline 1.8. In FIG. 20B is shown the summary for read 1 and the normalised GC bias curves (obtained by dividing the original GC bias curves by the curve at low density lane 1) are shown in FIG. 20C. A direct comparison in terms of density-dependent GC bias of dNTPs in formamide and water and sodium citrate in formamide, both with an ammonium-free Bst mix is shown in FIG. 20D.

FIG. 21A, FIG. 21B and FIG. 21C depict effect of sodium citrate concentration and betaine in formamide. The experiment design is shown in FIG. 21A. After seeding of a standard human library (CT3576) at high and low density and 1st strand extension with Phusion, clusters were amplified using either 35 cycles (with standard reagents, lanes 1 and 2) or 32 cycles of isothermal (with an ammonium-free Bst mix, lanes 3 to 8). After read 1 preparation the flowcell was sequenced with a GAIIx instrument. This particular experiment was a single read run using the 95G chemistry sequencing (36 cycles of SBS). Analysis was carried out with pipeline 1.8. FIG. 21B shows the summary for read 1 whereas the normalised GC bias curves (obtained by dividing the original GC bias curves by the curve at low density lane 1) are shown in FIG. 21C.

DEFINITIONS

Figure 1:
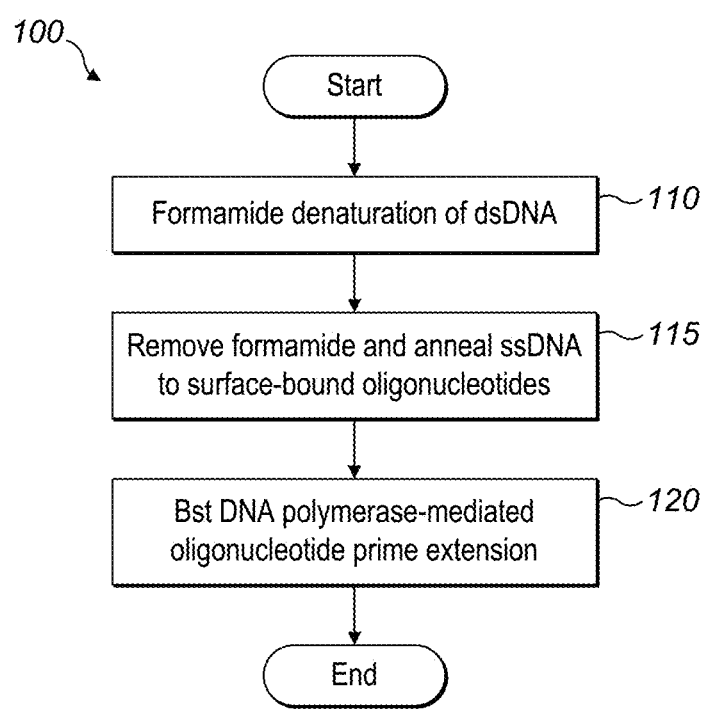
FIG. 1 illustrates a flow diagram of an example of an isothermal bridge amplification protocol for cluster amplification on a flow cell surface.

As used herein, the following terms have the meanings indicated.

The terms "normalize" or "reduce sequence specific bias" (e.g., reducing density-dependent GC bias) when used in reference to the amplification of nucleic acid templates, means to alter the ratio of molecules of different type obtained during an amplification process such that the number of molecules of a particular type in the population is made more equal to the number of molecules of another type in the population. Thus for an amplification reaction carried out on a population of nucleic acid templates of different sequence, to normalize the amplification can mean lowering any sequence specific biases which would otherwise result in certain members of the population increasing in number more than other members of the population. The normalization process can be used to produce relative ratios of the fragments in the population that are the same after the amplification as they were in the population before amplification. Thus for example a population comprising 1 million molecules of different sequence will contain, after amplification, on average the same number of copies of each of the 1 million fragments without any specific biases for certain sequences. It will be understood that this is a statistical measure and that the absence of bias can be within an acceptable variance such as within 0.5, 1, 2, 3, 4, 5, 10, 15, 20, 25, 30, 35, 40, 45 or 50% variance in the number of copies for each fragment. When carried out on a solid support to make nucleic acid clusters, the normalization of the amplification results in an array of clusters with a similar number of molecules in each cluster, and thus similar sizes and signal intensities.

The term "different" when used in reference to two or more nucleic acids means that the two or more nucleic acids have nucleotide sequences that are not the same. For example, two nucleic acids can differ due to one sequence being longer than the other and conversely one sequence being shorter than the other. Two nucleic acids can differ in the content and order of nucleotides in the sequence of one nucleic acid compared to the other nucleic acid, independent of any differences in sequence length between the two nucleic acids. The term can be used to describe nucleic acids whether they are referred to as copies, amplicons, templates, targets, primers, oligonucleotides, polynucleotides, or the like.

As described herein, nucleic acid templates containing a high level of A and T bases typically amplify more efficiently than nucleic acid templates with a high level of G and C bases. Nucleic acid templates with sequences containing a high level of A or T bases compared to the level of G or C bases are referred to throughout as AT rich templates or templates with high AT content. Accordingly, AT rich templates can have relatively high levels of A bases, T bases or both A and T bases. Similarly, nucleic acid templates with sequences containing a high level of G or C bases compared to the level of A or T bases are referred to throughout as GC rich templates or templates with high GC content. Accordingly, GC rich templates can have relatively high levels of G bases, C bases or both G and C bases. The terms GC rich and high GC content are used interchangeably. Similarly, the terms AT rich and high AT content are used interchangeably. The phrases GC rich and AT rich, as used herein, refer to a nucleic acid sequence having a relatively high number of G and/or C bases or A and/or T bases, respectively, in its sequence, or in a part or region of its sequence, relative to the sequence content contained within a control. In this case, the control can be similar nucleic acid sequences, genes, or the genomes from which the nucleic acid sequences originate. Generally, nucleic acid sequences having greater than about 52% GC or AT content are considered GC rich or AT rich sequences. Optionally, the GC content or AT content is greater than 55, 60, 65, 70, 75, 80, 85, 90, 95 or 99%. Nucleic acid sequences containing discrete regions of high GC to AT content may also be considered GC rich or AT rich, respectively. The methods provided herein normalize the efficiencies or levels of amplification of templates with different sequence, for example, with high AT and/or GC content.

The term "amplification cycle" refers to one or more steps of an amplification process that are sufficient to produce one or more copies of a nucleic acid template. By way of example, an amplification cycle includes providing one or more nucleic acid templates, denaturing the nucleic acid templates to produce single stranded nucleic acid templates, annealing one or more primers to the single stranded nucleic acid templates, and extending the primers to produce copies of the single stranded nucleic acid templates. As described herein, such cycles can be repeated one or more times under conditions favoring AT rich or GC rich templates. Thus, a cycle of amplification can include a unit of one or more steps that is repeated in a round of amplification.

As used throughout, the phrase "favoring AT rich templates" means that the efficiency of amplification of AT rich templates is not reduced or inhibited relative to non-AT rich templates. By way of example, under standard amplification conditions, AT rich templates amplify at a higher efficiency than GC rich templates. Thus, conditions favoring AT rich templates include standard amplification conditions. As used throughout, the phrase standard amplification conditions means amplifying a nucleic acid sequence under conditions including all standard reagents and conditions necessary to carry out amplification. Standard amplification conditions are known and described in, for example, Saiki et al., Science, 230:1350 (1985).

As used herein, the phrase "favoring GC rich templates" means that the efficiency of amplification of GC rich templates is increased relative to AT rich templates and/or the efficiency of amplification of AT rich templates is reduced relative to GC rich templates.

The nucleotides used in the amplification process may be ribo- or deoxyribo-nucleotides. The nucleotides used in the amplification may be nucleotide 5' polyphosphates, for example 5' triphosphates. The nucleotides used in the amplification reaction may be the four nucleotide triphosphates typically found in native DNA: dATP, dGTP, dCTP and dTTP.

As used herein, the terms high, higher, increase(s), increased, or increasing refer to any increase above a reference or control, unless stated otherwise. The terms low, lower, decrease(s), decreased, decreasing, reduce(s), reduced, reducing or reduction refer to any decrease below a reference or control, unless stated otherwise. By way of example, a control includes control values or control levels, which can be values or levels prior to, or in the absence of, a stimulus. A control or control value includes the level of efficiency of amplification of nucleic acid sequences under standard amplification conditions or can comprise a known value, level or standard. Thus, for example, a higher or lower value (e.g., temperature or concentration) as compared to a control refers to a value that is higher or lower than a known or arbitrarily set value.

The term "isothermal" refers to thermodynamic processes in which the temperature of a system remains constant: DT=0. This typically occurs when a system is in contact with an outside thermal reservoir (for example, heat baths and the like), and processes occur slowly enough to allow the system to continually adjust to the temperature of the reservoir through heat exchange.

The term "substantially isothermal" as used herein is intended to mean that the system is maintained at essentially the same temperature. The term is also intended to capture minor deviations in temperature which might occur as the system equilibrates, for example when components which are of lower or higher temperature are added to the system. Thus it is intended that the term includes minor deviations from the temperature initially chosen to perform the method and those in the range of deviation of commercial thermostats. Particularly the temperature deviation will be no more than about +/−2° C., more particularly no more than about +/−1° C., yet more particularly no more than about +/−0.5° C., no more than about +/−0.25° C., no more than about +/−0.1° C. or no more than about +/−0.01° C.

The term "amplifying" as used herein is intended to mean the process of increasing the numbers of a template polynucleotide sequence by producing one or more copies. Accordingly it will be clear that the amplification process can be either exponential or linear. In exponential amplification the number of copies made of the template polynucleotide sequence increases at an exponential rate. For example, in an ideal PCR reaction with 30 cycles, 2 copies of template DNA will yield 230 or 1,073,741,824 copies. In linear amplification the number of copies made of the template polynucleotide sequences increases at a linear rate. For example, in an ideal 4-hour linear amplification reaction whose copying rate is 2000 copies per minute, one molecule of template DNA will yield 480,000 copies.

The term "copy" when used in reference to a first nucleic acid molecule is intended to mean a second nucleic acid molecule having the same sequence as the first nucleic acid or the complementary sequence of the nucleic acid. The nucleic acids can be single stranded or double stranded. For example, a single stranded copy can have the same sequence of a single stranded template, a single stranded copy can have the complementary sequence of a single stranded template, a double stranded copy can include the same sequence and the complementary sequence (i.e. two strands) of a single stranded template, or a double stranded copy can include the same sequences as a double stranded template. Similarly, the term "copy" when used in reference to a nucleic acid sequence means the same sequence or the complementary sequence.

As used herein, the terms "polynucleotide", "oligonucleotide" or "nucleic acid" can refer to deoxyribonucleic acid (DNA), ribonucleic acid (RNA) or analogues of either DNA or RNA made, for example, from nucleotide analogues. The terms "polynucleotide", "oligonucleotide" or "nucleic acid" are applicable to single stranded (such as sense or antisense) and double stranded molecules. The terms "polynucleotide", "oligonucleotide" or "nucleic acid" as used herein also encompass cDNA, that is complementary or copy DNA produced from an RNA template, for example by the action of reverse transcriptase.

Single stranded polynucleotide molecules useful in a method or composition of the invention may have originated in single-stranded form, as DNA or RNA or may have originated in double-stranded DNA (dsDNA) form (e.g. genomic DNA fragments, PCR and amplification products and the like). Thus a single stranded polynucleotide may be the sense or antisense strand of a polynucleotide duplex. Methods of preparation of single stranded polynucleotide molecules suitable for use in the method of the invention using standard techniques are well known in the art.

The term "immobilized" or "bound" as used herein is intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilized or attached to a support under conditions in which it is intended to use the support, for example in applications requiring nucleic acid amplification and/or sequencing.

In many embodiments of the invention, amplification primers for solid phase amplification are immobilized by covalent attachment to a solid support at or near the 5' end of the primer, leaving the template-specific portion of the primer free to anneal to its cognate template and the 3' hydroxyl group free to function in primer extension. The chosen attachment chemistry will depend on the nature of the solid support, and any functionalization or derivitization applied to it. The primer itself may include a moiety, which may be a non-nucleotide chemical modification to facilitate attachment. In particular embodiments the primer may include a sulphur containing nucleophile such as phosphothioate or thiophosphate at the 5' end. In the case of solid supported polyacrylamide hydrogels, this nucleophile may bind to a bromoacetamide group present in the hydrogel. In a preferred embodiment the means of attaching the primers to the solid support is via 5' phosphothioate attachment to a hydrogel comprised of polymerised acrylamide and N-(5-bromoacetamidylpentyl) acrylamide (BRAPA). Such an arrangement is described more fully in co-pending application WO 05/065814, whose contents are incorporated herein by reference.

Single stranded template polynucleotide molecules may be attached to a solid support via hybridization to immobilized primers, or alternatively the single stranded polynucleotide molecules may also be directly attached to the solid support at or near the 5' end. The chosen attachment chemistry will depend on the nature of the solid support, and any functionalization or derivitization applied to it. The single stranded polynucleotide molecule itself may include a moiety, which may be a non-nucleotide chemical modification to facilitate attachment. In particular embodiments a single stranded polynucleotide molecule may include a sulphur containing nucleophile such as phosphorothioate or thiophosphate at the 5' end. In the case of solid supported polyacrylamide hydrogels, this nucleophile can also bind to the bromoacetamide groups present in the hydrogel. In one embodiment the means of attaching the single stranded polynucleotide molecule to the solid support is via 5' phosphorothioate attachment to a hydrogel comprised of polymerised acrylamide and N-(5-bromoacetamidylpentyl) acrylamide (BRAPA). Such an arrangement is described more fully in co-pending application WO 05/065814, whose contents are incorporated herein by reference.

The term "solid support" as used herein refers to any surface, inert substrate or matrix to which nucleic acids can be attached such as, for example, beads, including latex or dextran beads, a surface, such as a polystyrene or polypropylene surface, polyacrylamide gel, gold surfaces, glass surfaces and silicon wafers. The solid support may be a glass surface. The solid support may be a planar surface, although the invention also works on beads which are moved between containers of different buffers, or beads arrayed on a planar surface. The solid support can be a flow cell, resin, gel, bead, well, column, chip, membrane, matrix, plate or filter.

In certain embodiments the solid support may comprise an inert substrate or matrix which has been "functionalized", for example by the application of a layer or coating of an intermediate material comprising reactive groups which permit covalent attachment to molecules such as polynucleotides. By way of non-limiting example such supports may include polyacrylamide hydrogels supported on an inert substrate such as glass. In such embodiments the molecules (e.g. polynucleotides) may be directly covalently attached to the intermediate material (e.g. the hydrogel) but the intermediate material may itself be non-covalently attached to the substrate or matrix (e.g. the glass substrate). Such an arrangement is described more fully in co-pending application WO 05/065814, whose contents are included herein by reference.

Primer oligonucleotides or primers are polynucleotide sequences that are capable of annealing specifically to one or more single stranded polynucleotide template to be amplified under conditions encountered in the primer annealing step of each cycle of an amplification reaction. Generally amplification reactions can use at least two amplification primers, often denoted "forward" and "reverse" primers. In certain embodiments the forward and reverse primers may be identical. The forward primer oligonucleotides can include a "template-specific portion", being a sequence of nucleotides capable of annealing to a primer-binding sequence in at least one strand of the molecule to be amplified. Reverse primer oligonucleotides can include a template specific portion capable of annealing to the complement of the strand to which the forward primer anneals during the annealing step. Generally primer oligonucleotides are single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand.

Primers may additionally comprise non-nucleotide chemical modifications, again provided that such modifications do not permanently prevent primer function. Chemical modifications may, for example, facilitate covalent attachment of the primer to a solid support. Certain chemical modifications may themselves improve the function of the molecule as a primer, or may provide some other useful functionality, such as providing a site for cleavage to enable the primer (or an extended polynucleotide strand derived therefrom) to be cleaved from a solid support.

Although the invention may encompass solid-phase amplification methods, in which only one amplification primer is immobilized on a solid support (the other primer usually being present in free solution), in a particular embodiment, the solid support may be provided with both the forward and reverse primers immobilized. In practice there can be a plurality of identical forward primers and/or a plurality of identical reverse primers immobilized on the solid support, for example, in embodiments wherein the amplification process utilizes an excess of primers to sustain amplification. Thus references herein to forward and reverse primers are to be interpreted accordingly as encompassing a plurality of such primers unless the context indicates otherwise.

"Solid-phase amplification" as used herein refers to any nucleic acid amplification reaction carried out on or in association with a solid support such that all or a portion of the amplified products are immobilized on the solid support. In particular, the term encompasses solid phase amplification reactions analogous to standard solution phase PCR except that one or both of the forward and reverse amplification primers is/are immobilized on the solid support.

Primer oligonucleotides and single stranded polynucleotide molecules that have been immobilized on a solid support at a desired density can be used to generate extension products by carrying out an appropriate number of cycles of amplification on the covalently bound single stranded polynucleotide molecules so that each colony, or cluster comprises multiple copies of the original immobilized single stranded polynucleotide molecule (and its complementary sequence). One cycle of amplification can include steps of hybridization, extension and denaturation. Such steps are generally comparable with the steps of hybridization, extension and denaturation of PCR.

In embodiments utilizing solid phase amplification, suitable conditions can be applied to a single stranded polynucleotide molecule and a plurality of immobilized primer oligonucleotides such that sequence Z at the 3' end of the single stranded polynucleotide molecule hybridizes to a primer oligonucleotide sequence X to form a complex wherein, the primer oligonucleotide hybridizes to the single stranded template to create a "bridge" structure. Suitable conditions such as neutralizing and/or hybridizing buffers are well known in the art (See Sambrook et al., Molecular Cloning, A Laboratory Manual, 3rd Ed, Cold Spring Harbor Laboratory Press, NY; Current Protocols, eds Ausubel et al.). The neutralizing and/or hybridizing buffer may then be removed. One suitable hybridization buffer is referred to as "amplification pre-mix", and contains 2 M Betaine, 20 mM Tris, 10 mM Ammonium Sulfate, 2 mM Magnesium sulfate, 0.1% Triton, 1.3% DMSO, pH 8.8.

By applying suitable conditions, an extension reaction can be performed for a complex formed between immobilized primer and single stranded polynucleotide template. The primer oligonucleotide of the complex can be extended by sequential addition of nucleotides to generate an extension product complementary to the single stranded polynucleotide molecule.

Examples of enzymes with polymerase activity which can be used in the present invention are DNA polymerase (Klenow fragment, T4 DNA polymerase, Bst polymerase), heat-stable DNA polymerases from a variety of thermostable bacteria (such as Taq, VENT, Pfu, Tfl, Phusion DNA polymerases) as well as their genetically modified derivatives (TaqGold, VENTexo, Pfu exo). A combination of RNA polymerase and reverse transcriptase can also be used to generate the extension products. A useful polymerase enzyme can have strand displacement activity. The polymerase enzyme can be active at a pH of about 7 to about 9, particularly pH 7.9 to pH 8.8. The nucleoside triphosphate molecules used can be deoxyribonucleotide triphosphates, for example dATP, dTTP, dCTP, dGTP, or they can be ribonucleoside triphosphates for example ATP, UTP, CTP, GTP. The nucleoside triphosphate molecules may be naturally or non-naturally occurring. An amplification reaction may also contain additives such as DMSO and or Betaine, for example, to normalise the melting temperatures of the different sequences in the template strands. A suitable solution for initial cycles of extension is referred to as "amplification mix" and contains 2 M betaine, 20 mM Tris, 10 mM Ammonium Sulfate, 2 mM Magnesium sulfate, 0.1% Triton, 1.3% DMSO, pH 8.8 plus 200 μM dNTPs and 80 units/mL of Bst polymerase.

The denaturation can be carried out using heat or by using a denaturing buffer. Suitable denaturing buffers are well known in the art (See Sambrook et al., Molecular Cloning, A Laboratory Manual, 3rd Ed, Cold Spring Harbor Laboratory Press, NY; Current Protocols, eds. Ausubel et al.). By way of example it is known that alterations in pH and low ionic strength solutions can denature nucleic acids at substantially isothermal temperatures. Formamide and urea can be used for denaturation. In a particular embodiment the concentration of formamide is 50% or more, and may be used neat. Such conditions result in denaturation of double stranded nucleic acid molecules to single stranded nucleic acid molecules. Alternatively or additionally, the strands may be separated by treatment with a solution of very low salt (for example less than 0.1 mM cationic conditions) and high pH (>12) or by using a chaotropic salt (e.g. guanidinium hydrochloride). In a particular embodiment, a strong base may be used. A strong base is a basic chemical compound that is able to deprotonate very weak acids in an acid base reaction. The strength of a base is indicated by its pKb value. Compounds with a pKb value of less than about 1 are called strong bases and are well known to a skilled practitioner. In a particular embodiment the strong base is Sodium Hydroxide (NaOH) solution used at a concentration of from 0.05 M to 0.25 M. More particularly NaOH is used at a concentration of 0.1 M.

It may be advantageous to perform optional washing steps in between steps of an amplification method. For example, an extension buffer without polymerase enzyme with or without dNTPs could be applied to a solid support upon which amplification is being carried out and it can be applied before being removed and replaced with complete extension buffer (extension buffer that includes all necessary components for extension to proceed).

Multiple cycles of amplification on a solid surface under conditions exemplified above can result in a nucleic acid colony or "cluster" comprising multiple immobilized copies of a particular single stranded polynucleotide sequence and its complementary sequence. Initial immobilization of a single stranded polynucleotide molecule under conditions exemplified herein can result in the single stranded polynucleotide molecule only hybridizing with primer oligonucleotides located at a distance within the total length of the single stranded polynucleotide molecule. Thus, the boundary of the nucleic acid colony or cluster formed can be limited to a relatively local area, namely the area in which the initial single stranded polynucleotide molecule was immobilized. If conditions are used wherein the templates and the complementary copies thereof remain immobilized throughout the whole amplification process, then the templates do not become intermingled other than by becoming large enough to overlap on the surface. In particular embodiments, there is no non-immobilized nucleic acid during any part of the amplification process, and thus the templates cannot diffuse and initiate further clusters elsewhere on the surface.

Hybridization, extension and denaturation steps of an amplification method set forth herein may all be carried out at the same, substantially isothermal temperature. Preferably the temperature is from 37° C. to about 75° C., depending on the choice of enzyme, more preferably from 50° C. to 70° C., yet more preferably from 60° C. to 65° C. for Bst polymerase. In a particular embodiment the substantially isothermal temperature may be around the melting temperature of the oligonucleotide primer(s). Methods of calculating appropriate melting temperatures are known in the art. For example the annealing temperature may be about 5° C. below the melting temperature (Tm) of the oligonucleotide primers. In yet another particular embodiment the substantially isothermal temperature may be determined empirically. The temperature can be that at which the oligonucleotide displays greatest specificity for the primer binding site whilst reducing non-specific binding.

The term "common sequence," when used in reference to a collection of nucleic acid molecules, means a sequence that is the same for all of the nucleic acids in the collection. The nucleic acids in the collection can have a region of common sequence despite the presence of at least one other region in each of the nucleic acids that differs between the nucleic acids in the collection. As exemplified by the embodiments set forth above, all templates within a 5' and 3' modified library can contain regions of common sequence Y and Z at (or proximal to) their 5' and 3' ends, particularly wherein the common sequence at the 5' end of each individual template in the library is not identical and not fully complementary to the common sequence at the 3' end of said template. The term "library" refers to a collection or plurality of template molecules which can share common sequences at their 5' ends and common sequences at their 3' ends. Use of the term "5' and 3' modified library" to refer to a collection or plurality of template molecules should not be taken to imply that the templates making up the library are derived from a particular source. By way of example, a "5' and 3' modified library" can include individual templates within the library that have the same nucleotide sequence or that have different nucleotide sequences. Furthermore, the templates can, but need not be related in terms of sequence and/or source.

In various embodiments the invention can encompass use of so-called "mono-template" libraries, which comprise multiple copies of a single type of template molecule, each having common sequences at their 5' ends and their 3' ends, as well as "complex" libraries wherein many, if not all, of the individual template molecules comprise different target sequences, although all share common sequences at their 5' ends and 3' ends. Such complex template libraries may be prepared from a complex mixture of target polynucleotides such as (but not limited to) random genomic DNA fragments, cDNA libraries etc. The invention may also be used to amplify "complex" libraries formed by mixing together several individual "mono-template" libraries, each of which has been prepared separately starting from a single type of target molecule (i.e., a mono-template). In particular embodiments more than 50%, or more than 60%, or more than 70%, or more than 80%, or more than 90%, or more than 95% of the individual polynucleotide templates in a complex library may comprise different target sequences, although all templates in a given library can share a common sequence at their 5' ends and a common sequence at their 3' ends.

Additives described herein are related at least for their ability to normalize amplification of nucleic acid templates of different sequences. The methods optionally include the use of different concentrations of nucleotides and/or nucleotide analogs as described herein. The additives may be, for example, ethylene glycol, polyethylene glycol, 1,2-propanediol, dimethyl sulfoxide (DMSO), glycerol, formamide, 7-deaza-GTP, acetamide, tetramethyl ammonium chloride (TMACl), salt or Betaine. For example, Betaine (carboxymethyl trimethyl ammonium ($(CH_3)_3N^+CH_2COO^-$)) may be added to the amplification mix in order to normalize the amplification of different template sequences. Optionally, a combination of Betaine and DMSO or a combination of Betaine, DMSO and 7-deaza-dGTP is used. In particular, concentrations of Betaine may be above 2 Molar (M), for example, between 2 and 5 M, between 2.5 and 4 M or between 2.75 and 3.75 M Description The present invention provides methods of reducing density-dependent GC bias in isothermal bridge amplification used for cluster generation. In one embodiment, the method of the invention uses the addition of an additive to a first solution in an isothermal bridge amplification protocol. In one example, the first solution in the bridge amplification protocol is a formamide solution used to denature dsDNA. In one embodiment, the first solution further comprises EDTA. In one example, the additive is a mixture of dNTPs. In another example, the additive is a single dNTP (i.e., dATP, dCTP, dGTP, or dTTP). In yet another example, the additive is 10 mM trisodium citrate. In one embodiment, the additive is 1 mM trisodium citrate. In one embodiment, the additive is less than 1 mM trisodium citrate.

In another embodiment, the method of the invention uses the addition of an additive to a second solution in an isothermal bridge amplification protocol. In one example, the second solution in the bridge amplification protocol is a pre-mix solution. In one example, the additive is a mixture of dNTPs. In another example, the second solution in the bridge amplification protocol is water. In this example, water may be used alone or with the addition of dNTPs, trisodium citrate and/or other additive. Replacing the pre-mix solution, which contains salts and buffers, with water enhances amplification of GC-rich templates. An isothermal bridge amplification protocol for cluster generation on a flow cell typically includes repeated cycles of denaturation, annealing, and extension. FIG. 1 illustrates a flow diagram of an example of an isothermal bridge amplification protocol 100 for cluster amplification on a flow cell surface. In one example, bridge amplification protocol 100 is performed at about 60° C. and is repeated any number of times (e.g., typically 35 times) to generate a clonal population of identical DNA strands for each seeded DNA template. For example, the bridge amplification protocol may be repeated for one to fifty, one to twenty-five, one to fifteen, or one to ten cycles of amplification. Bridge amplification protocol 100 includes, but is not limited to, the following steps.

At a step 110, a first solution, e.g., formamide (e.g., about 28 μL), is pumped through each lane of the flow cell seeded with DNA template. The formamide denatures the double-stranded cluster DNA on the flow cell to ssDNA.

At a step 115, the formamide is removed by pumping a second solution, e.g., a solution of cluster pre-mix (e.g., about 28 μL), through each lane of the flow cell. In one example, the pre-mix solution is a standard pre-mix solution comprising 20 mM Tris-HCl pH 8.8 @ 25° C., 10 mM ammonium sulfate, 2 mM Mg sulfate, 0.1% Triton X-100, 1.3% DMSO, and 2 M Betaine. Upon removal of formamide by washing with the pre-mix solution, the denatured DNA strands bridge over and anneal to oligonucleotide primers bound to the flow cell surface.

At a step 120, a third solution, e.g., a solution of Bst mix (e.g., about 36 μL), is pumped into each lane of the flow cell. The Bst mix contains dNTPs and Bst DNA polymerase. In one example, a standard Bst mix solution is 20 mM Tris-HCl pH 8.8 @ 25° C., 10 mM ammonium sulfate, 2 mM Mg sulfate, 0.1% Triton X-100, 1.3% DMSO, 2 M Betaine, 200 μM of each nucleotide, and 79 or 80 U/mL Bst polymerase. In another example, the Bst mix is an ammonium sulfate-free (NH4-free) Bst mix of 20 mM Tris-HCl pH 8.8 @ 25° C., 2 mM Mg sulfate, 0.1% Triton X-100, 1.3% DMSO, 2 M Betaine, 200 μM of each nucleotide, and 79 or 80 U/mL Bst polymerase. In the presence of the Bst mix, the surface-bound oligonucleotide primers that are hybridized to template molecules are fully extended.

Bridge amplification protocol 100 may be repeated any number of times. From a seeding site, a DNA molecule generates a cluster that is increased in size at every amplification cycle. However, for any particular insert length (DNA template length), cluster size and intensity may be affected by the GC composition of the insert. For example, DNA templates that contain a high proportion of A and T (or T and U for RNA) nucleotides tend to produce larger brighter clusters compared to templates that have a higher proportion of G and C nucleotides.

Figure 2A:
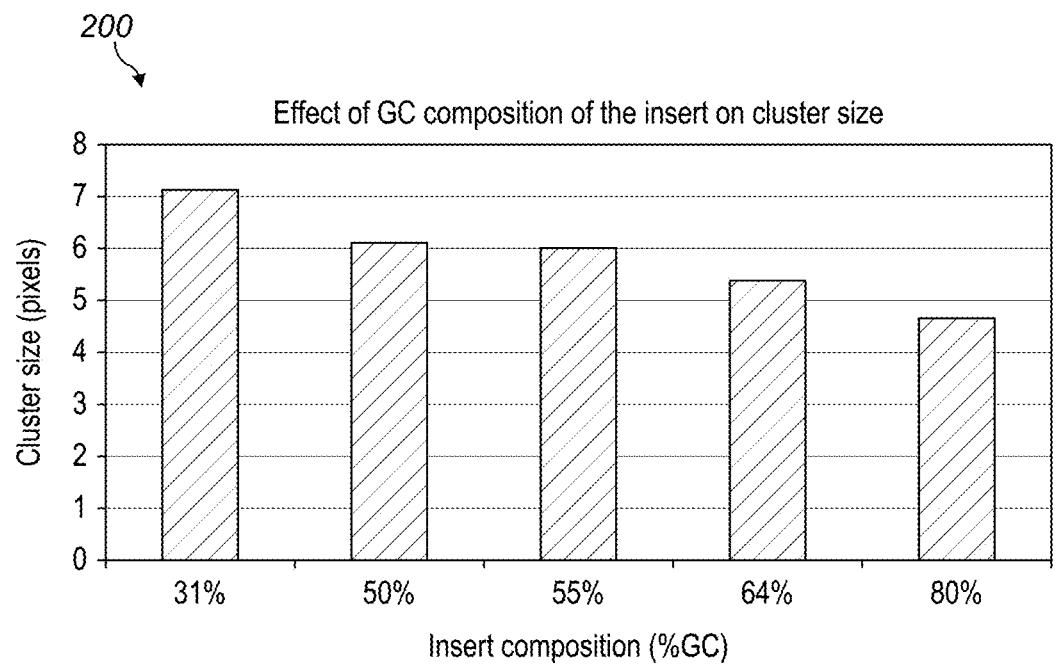
FIG. 2A and FIG. 2B show a plot of cluster size and a plot of cluster intensity, respectively, of clusters generated from monotemplates with a 400 bp insert with different GC composition.
Figure 2B:
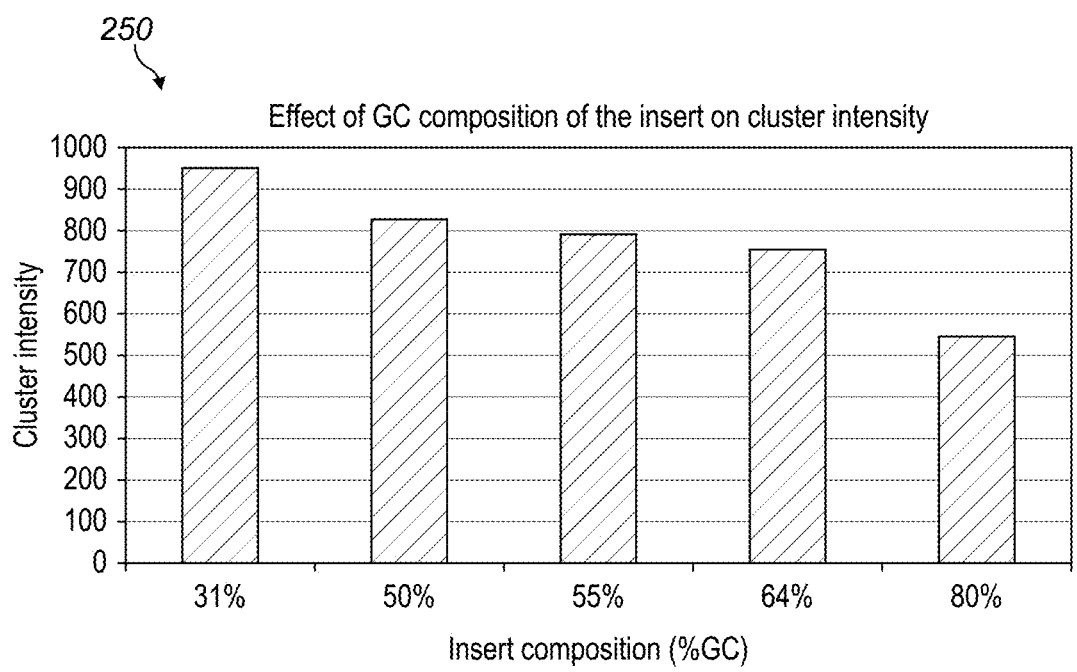

FIGS. 2A and 2B show a plot 200 of cluster size and a plot 250 of cluster intensity, respectively, of clusters generated from monotemplates with different GC composition. A monotemplate may be defined as a single sequencing-ready template sequence (e.g., P5 primer, sequencing primer, template insert, and P7 primer) with a certain insert size. In this example, monotemplates CT151 (31% GC), CT161 (50% GC), CT159 (55% GC), CT152 (64% GC), and CT180 (80% GC) with an insert of 400 bp in size were seeded in different lanes of the same flow cell. After a first extension, clusters were generated using 35 cycles of isothermal amplification. The flow cell was then stained with SYBR® Green and two representative tiles for each lane were imaged using a microscope. Cluster size and intensities were determined using image analysis software Firecrest.

Figure 3:
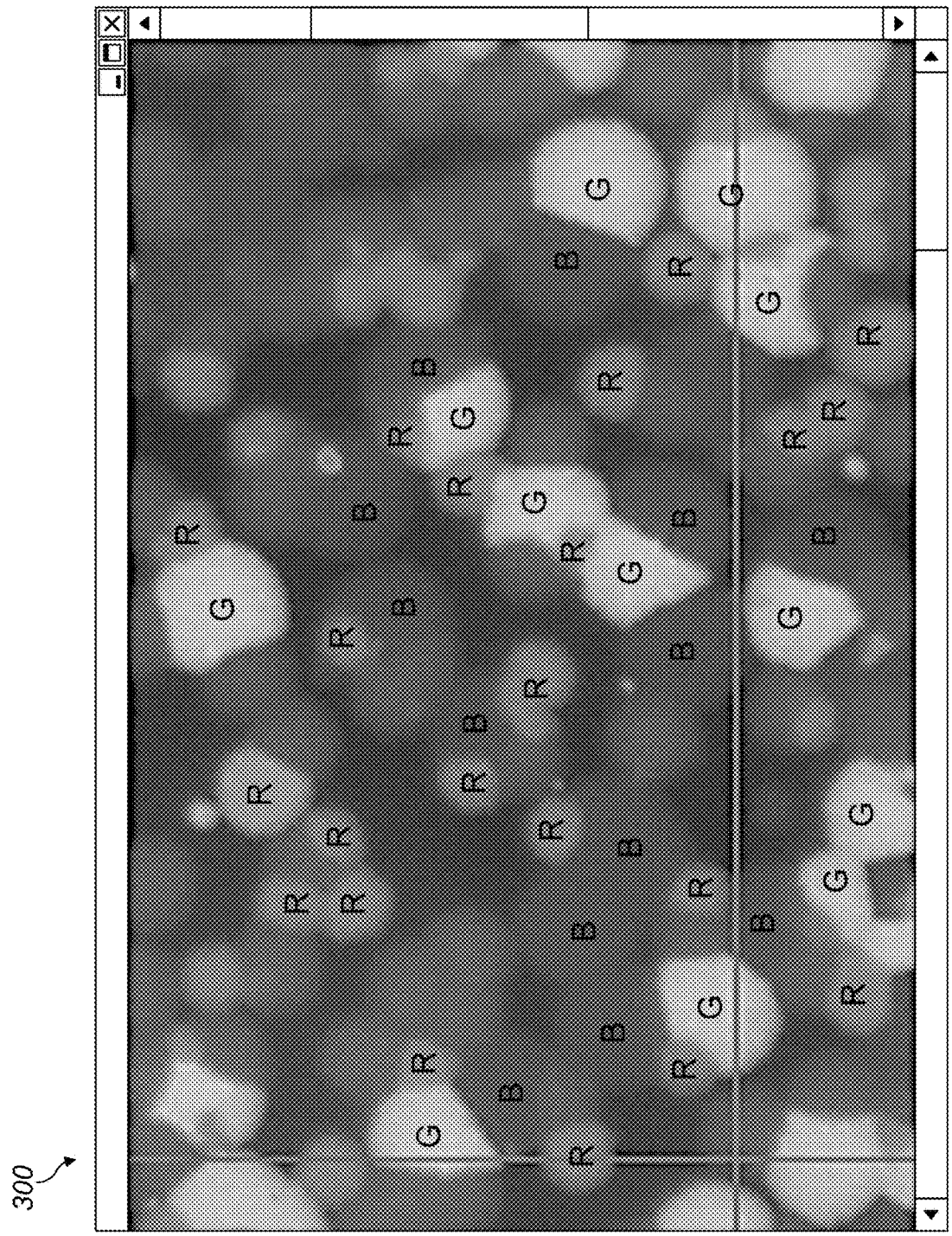
FIG. 3 shows a screenshot of a cluster image showing GC-rich clusters and AT-rich clusters, wherein four monotemplates were seeded at relatively low density.

FIG. 3 shows a screenshot 300 of a cluster image showing GC-rich clusters and AT-rich clusters. In this example, four monotemplates were seeded at relatively low density. Clusters were generated by over-amplifying each molecule in order to generate larger clusters. After linearization, 3' end blocking with ddNTPs, and hybridization of the sequencing primer, a first bridge amplification cycle was performed. A 3-color overlay image was then produced. Of the four monotemplates seeded, three were AT-rich (clusters from the third AT rich monotemplate are not shown) and one was GC rich (80% GC). The clusters are labelled in the grayscale image as AT rich "G" and "B", and GC rich "R". Because of contact inhibition, clusters do not overlap with one another; they stop growing when they come into contact. In the current amplification protocol, AT rich templates tend to produce large clusters, whereas GC rich templates give origin to smaller clusters. As shown in FIG. 3, GC rich clusters (R) have been squeezed between AT rich clusters (G and B) and their growth has been restricted by the faster growing AT rich clusters.

A decrease in cluster amplification efficiency of GC-rich clusters may be due to DNA damage caused by cluster amplification reagents. When a DNA strand is damaged (e.g., either broken phosphate-sugar backbone or damaged bases that stall primer extension) it may not act as template in subsequent amplification cycles and consequently, less efficient cluster amplification (i.e. smaller dimmer clusters) may be observed.

Modification of cluster amplification reagents by the addition of additives and/or the elimination of some components of the standard amplification reagent solutions may be used to ameliorate the DNA damage effects. This may be achieved by reduction of DNA damage by formamide by using an additive in the formamide solution, pre-mix solution, or both. Further, lowering the salt concentration may boost GC rich cluster growth through a mechanism that does not involve DNA damage. These results were surprising, It was previously unrecognised that formamide was causing DNA damage.

Figure 4:
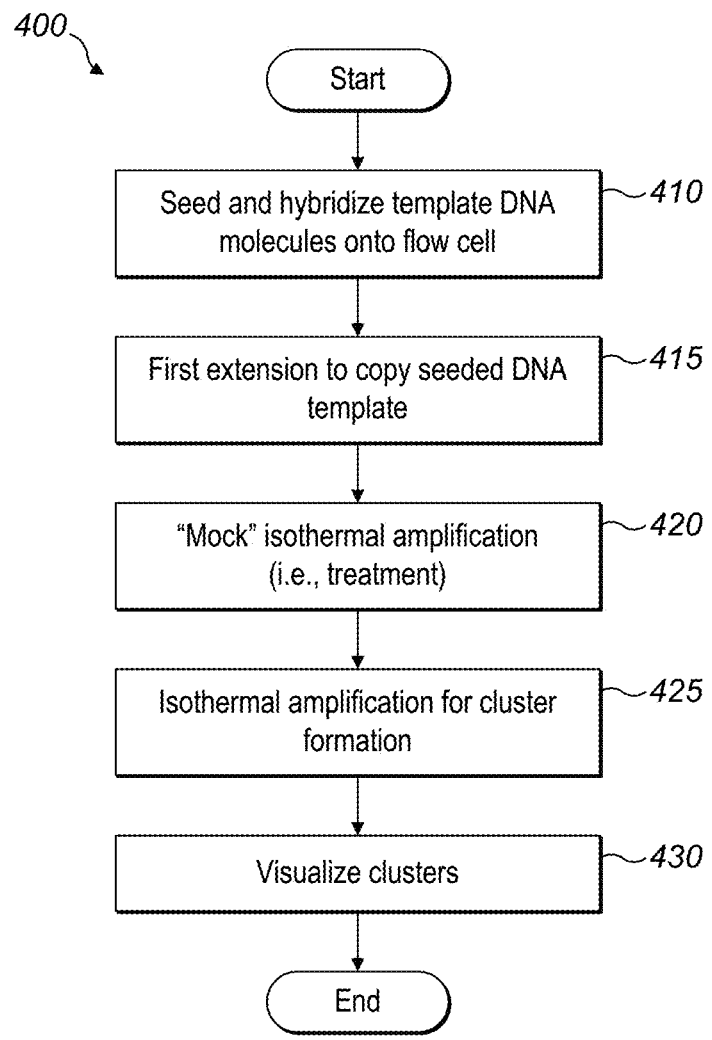
FIG. 4 illustrates a flow diagram of an example of a DNA damage assay for evaluating the effect of cluster amplification reagents and/or the addition of additives on cluster generation during isothermal bridge amplification.
Figure 5:
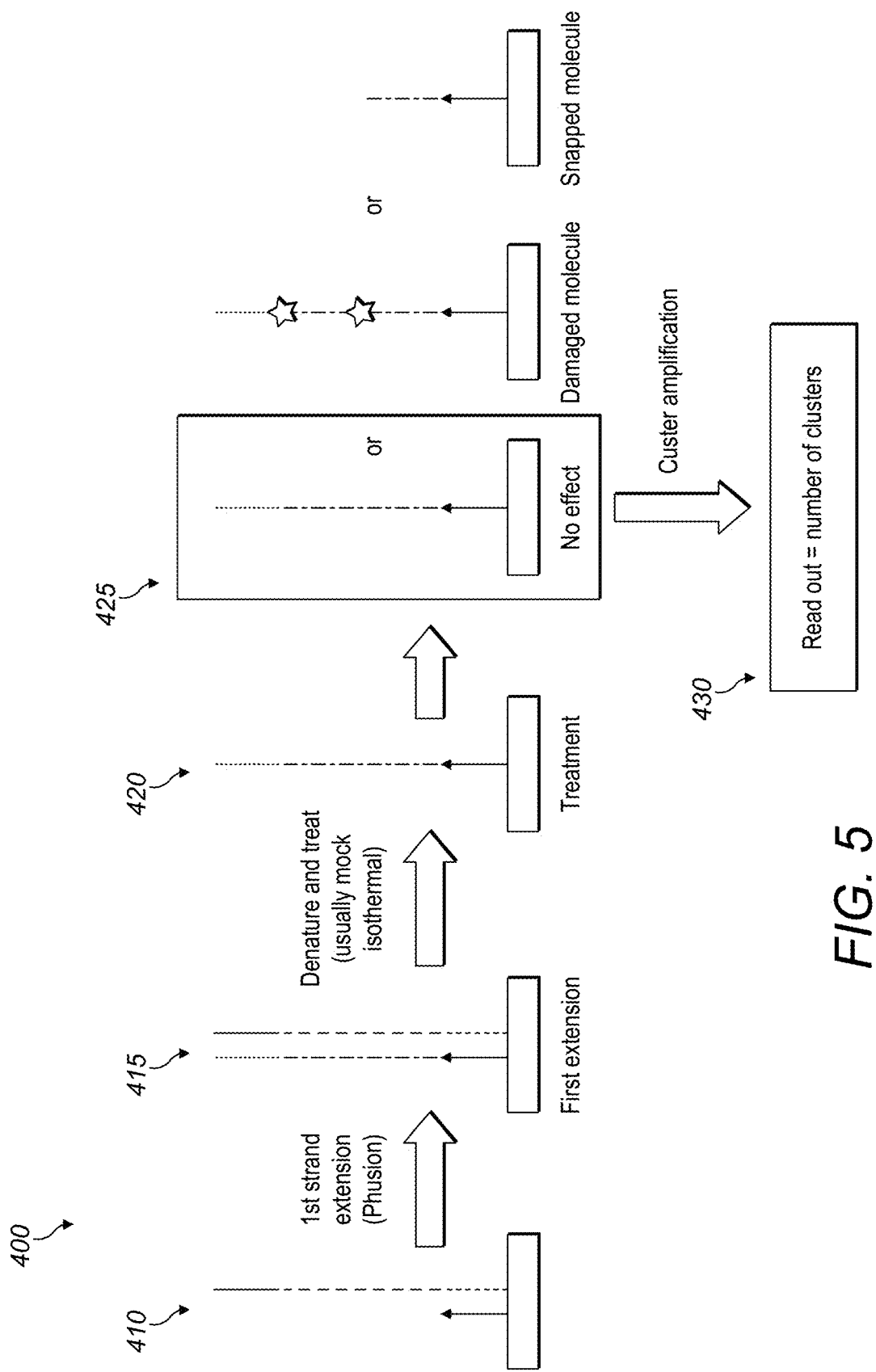
FIG. 5 shows pictorially the steps of the DNA damage assay of FIG. 4.

FIG. 4 illustrates a flow diagram of an example of a DNA damage assay 400 for evaluating the effect of cluster amplification reagents and/or the addition of additives on cluster generation during isothermal bridge amplification. FIG. 5 shows pictorially the steps of DNA damage assay 400 of FIG. 4. Method 400 includes, but is not limited to, the following steps.

At a step 410, template DNA molecules are seeded onto the flow cell and hybridized to surface-bound oligonucleotide primers. This step is also shown pictorially in FIG. 5.

At a step 415, the template DNA molecules are copied (first extension) using DNA polymerase (e.g., Taq DNA polymerase or Phusion DNA polymerase) and the seeded template strand is then removed by flowing 0.1 M NaOH through the flow cell (NaOH will also denature the DNA polymerase). Single stranded DNA molecules remain covalently bound to the flow cell surface. This step is also shown pictorially in FIG. 5.

At a step 420, single stranded DNA molecules covalently bound to the flow cell surface are subjected to a treatment of "mock" isothermal amplification. The mock isothermal amplification comprises cycling the reagents that are used in cluster amplification (e.g., formamide, pre-mix, and amplification mix with the omission of Bst DNA polymerase to avoid DNA amplification during treatment). In one example, the mock isothermal amplification comprises flowing formamide through a lane on the flow cell, removing the formamide by flowing pre-mix through the lane of the flow cell, and flowing a pre-mix containing dNTPs onto the flow cell lane. Included on the flow cell is a control lane which serves as negative control (no DNA damage). For the control lane, a wash buffer (0.3×SSC containing 0.1% Tween-20) is continuously flowed through the lane; the wash buffer is non-DNA damaging. This step is also shown pictorially in FIG. 5.

At a step 425, all lanes are rinsed with wash buffer and then subjected to isothermal amplification. Only non-damaged molecules can act as a template during this isothermal amplification step and therefore lead to cluster formation. Damaged DNA molecules or snapped molecules will not be amplified. This step is also shown pictorially in FIG. 5.

At a step 430, clusters are visualized by staining with a DNA binding dye (e.g., SYBR® Green) and imaged (e.g., three tiles for each lane) using a microscope and a camera. Image analysis software (e.g., Firecrest software) is used to determine numbers of clusters. By counting the number of clusters from each lane, it is possible to infer how many molecules have been damaged by a particular treatment.

Potential DNA damage caused by standard isothermal amplification reagents were evaluated using DNA damage assay 400 of FIG. 4 and seeded monotemplates. In one example, a CT180 monotemplate may be used in DNA damage assay 400 to evaluate potential DNA damage caused by isothermal amplification reagents. The CT180 monotemplate comprises 80% GC (i.e., it is GC rich) and has an insert size of 400 bp.

Figure 6:
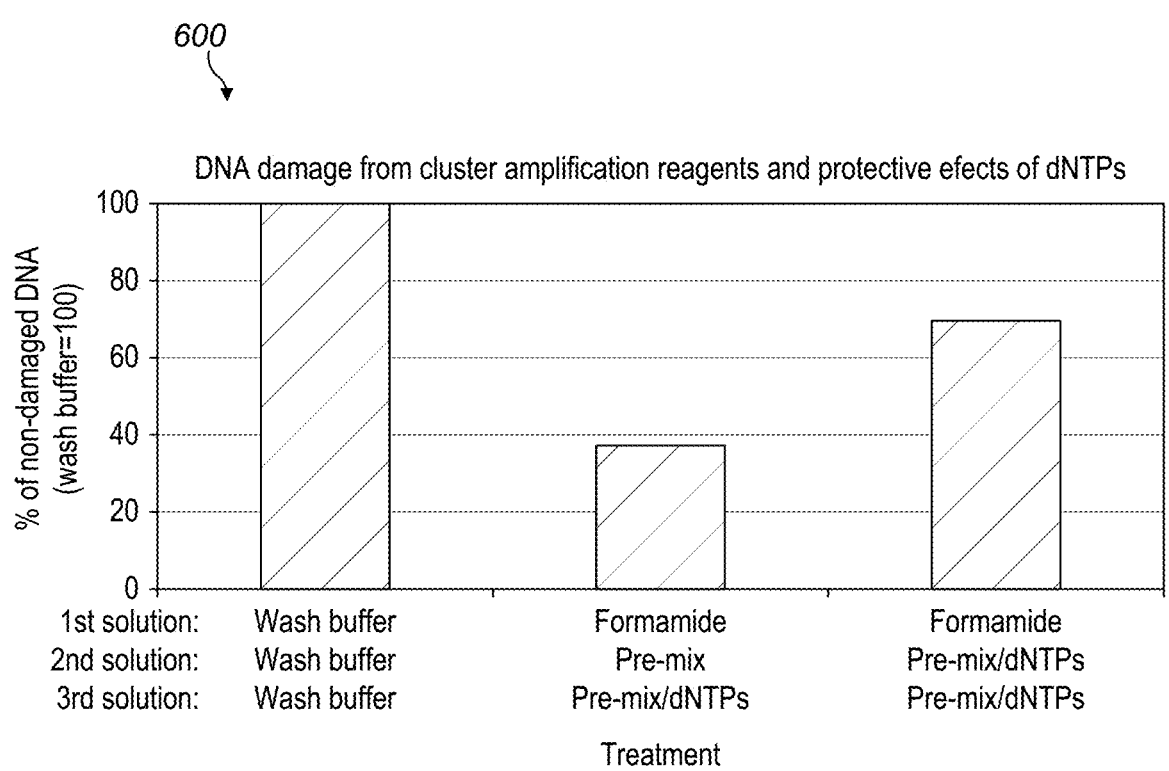
FIG. 6 shows a bar graph of the percentage of non-damaged DNA molecules in samples treated with formamide, pre-mix, and/or pre-mix plus dNTPs, compared to a lane treated with wash buffer only and evaluated using the DNA damage assay of FIG. 4.

FIG. 6 shows a bar graph 600 of the percent of non-damaged DNA molecules in samples treated with formamide, pre-mix, and/or pre-mix plus dNTPs and evaluated using DNA damage assay 400 of FIG. 4. In this experiment, monotemplate CT180 was seeded at 1 pM. After first strand extension with Taq DNA polymerase and template denaturation with NaOH, single DNA molecules were treated with 26 cycles of mock isothermal amplification (step 420 of DNA damage assay 400 of FIG. 4) using a first solution of 28 µL of formamide, a second solution of 28 µL of pre-mix without or with the addition of dNTPs, and a third solution of 36 µL of pre-mix with the addition of dNTPs. Each bar on the graph represents a lane on the flow cell. The control lane (first graph bar) was treated with wash buffer for the entire duration of the treatment (26 cycles). Cluster numbers for each treated lane (graph bars 2 and 3) on the flow cell are divided by the cluster number from the control lane and are expressed as a percentage of the control (reference) lane. Lane 2, which was treated with 26 cycles of mock isothermal amplification using the standard conditions (formamide/pre-mix/premix with dNTPs) shows a significant decrease in the number of clusters demonstrating that the isothermal amplification reagents cause DNA damage (a primer-density assay experiment showed that there was no significant loss of surface or oligonucleotides from the surface, data not shown). When dNTPs were included in the pre-mix solution (pre-mix/dNTPs) that was pumped immediately after formamide, DNA damage was less severe (compare lanes 2 and 3). These results suggest that dNTPs are protecting DNA from damage caused by cluster amplification reagents (e.g., formamide).

Figure 7:
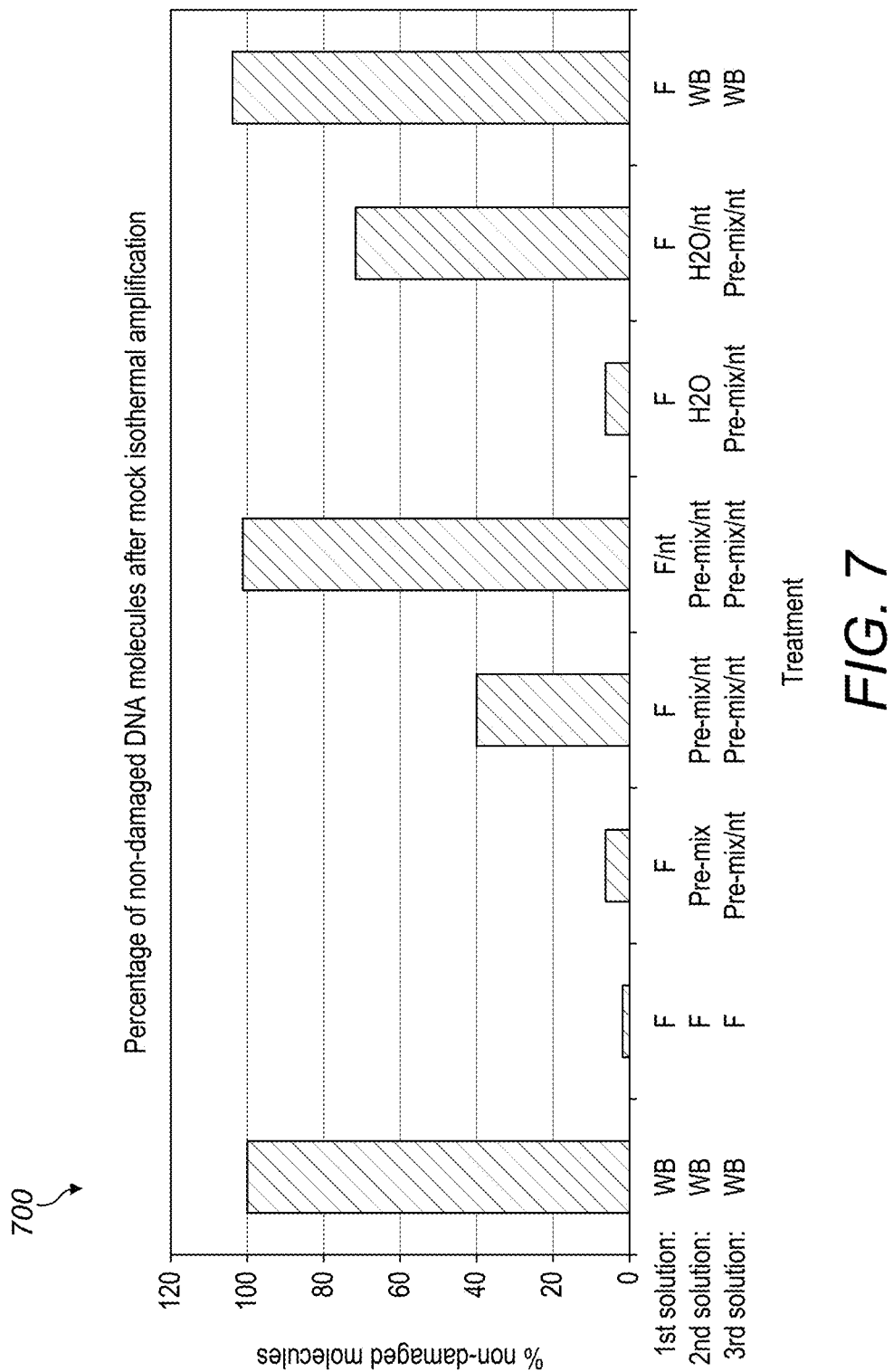
FIG. 7 shows a bar graph of the percentage of non-damaged DNA molecules in samples treated with formamide±dNTPs, pre-mix±dNTPs, or water±dNTPs and evaluated using the DNA damage assay of FIG. 4.

FIG. 7 shows a bar graph 700 of the percent of non-damaged DNA molecules in samples treated with formamide±dNTPs, pre-mix±dNTPs, or water±dNTPs and evaluated using DNA damage assay 400 of FIG. 4. In this experiment, monotemplate CT180 was seeded at 1 pM. After first strand extension with Taq DNA polymerase and template denaturation with NaOH, single DNA molecules were treated with 26 cycles of mock isothermal amplification (step 420 of DNA damage assay 400 of FIG. 4) using three solutions. The first solution was either 28 µL of wash buffer (WB), formamide (F), or formamide plus dNTPs (F/nt). The second solution was either 28 µL of wash buffer (WB), formamide (F), pre-mix, pre-mix plus dNTPs (pre-mix/nt), water (H2O), or water plus dNTPs (H2O/nt). The third solution was 36 µL of wash buffer (WB) or pre-mix/nt. dNTPs were used at a final concentration of 200 µM each. Each bar on the graph represents a lane of the flow cell. The data show the protective effect of dNTPs when present in the pre-mix solution (comparing lanes 3 and 4), in formamide (comparing lanes 4 and 5), and in water (comparing lanes 6 and 7). Lane 8 also shows that the wash buffer is also protecting the DNA molecules from damage caused by formamide (compare lanes 2 and 8).

Figure 8:
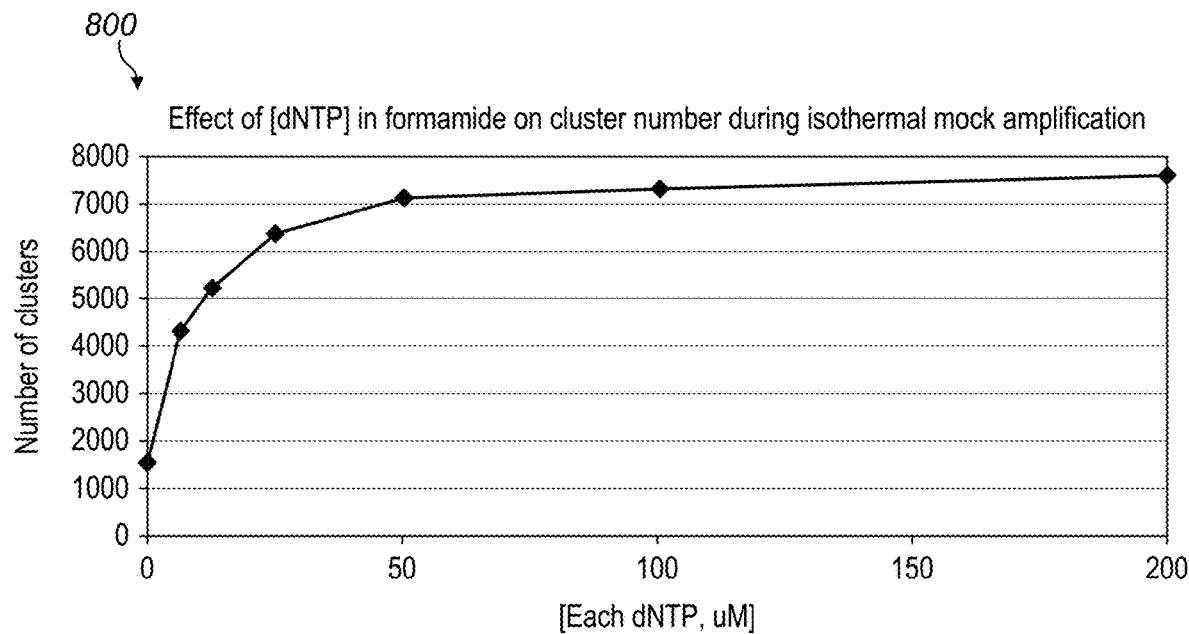
FIG. 8 shows a dose response curve of the effect of dNTP concentration in formamide on cluster number during mock isothermal amplification.

The effect of dNTP concentration on reducing formamide-induced DNA damage was evaluated in a titration experiment in which different amount of dNTPs were added to formamide. FIG. 8 shows a dose response curve 800 of the effect of dNTP concentration in formamide on cluster number during isothermal mock amplification. In this experiment, CT180 was seeded at 0.6 pM. First strand extension was performed using Taq DNA polymerase followed by NaOH denaturation. Single molecules were subsequently treated with 26 cycles of mock isothermal amplification according to DNA damage assay 400 of FIG. 4 using 28 µL of a first solution of formamide with different dNTP concentrations, 28 µL of a second solution of water with the same concentrations of dNTPs, and 36 µL of a third solution of pre-mix with the same concentrations of dNTPs. After the mock isothermal amplification, clonal populations of molecules (clusters) were generated with 26 cycles of isothermal amplification using 28 µL of formamide followed by 64 µL of B st mix in each cycle (no pre-mix was used). The results show a dose response of DNA damage abrogation with higher concentrations of dNTPs being more effective at preventing DNA damage.

Figure 9:
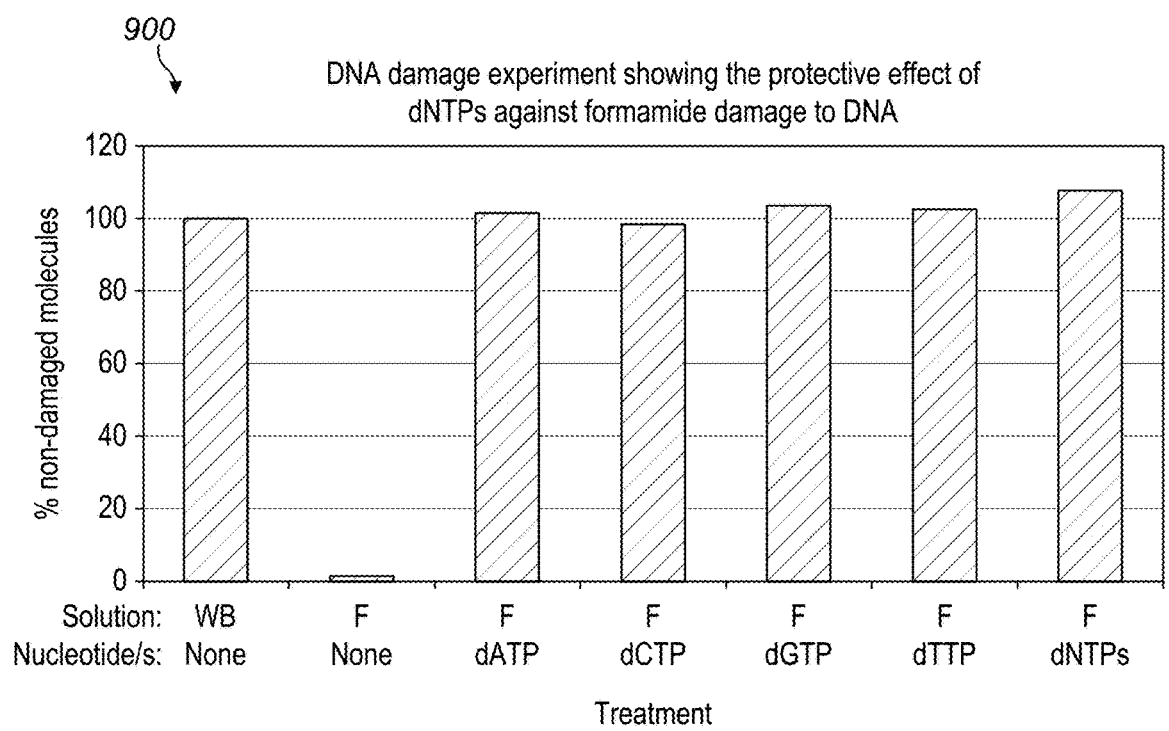
FIG. 9 shows a bar graph of the effectiveness of each dNTP to prevent DNA damage when used as a formamide additive.

The effect of individual dNTPs on reducing formamide-induced DNA damage was evaluated using DNA damage assay 400 of FIG. 4. FIG. 9 shows a bar graph 900 of the effectiveness of each dNTP to prevent DNA damage when used as a formamide additive. In this experiment, CT180 was seeded at 0.6 pM. First strand extension was performed using Taq DNA polymerase followed by NaOH denaturation. Single molecules were subsequently treated with either wash buffer (WB), formamide (F), or formamide plus dATP, dCTP, dGTP, dTTP, or a dNTP mix for 80 minutes at 60° C. (a time period that is similar to the duration of 26 cycles of isothermal amplification). After treatment, cluster amplification was performed using 26 isothermal cycles of 28 µL formamide followed by 64 µL of Bst mix for each cycle. The final concentration of the individual nucleotides was 800 µM. The concentration of each nucleotide in the dNTP mix was 200 µM. The data show that all four nucleotides are equally effective at protecting DNA from damage. The results also show that dNTPs prevent DNA damage caused by formamide when this chemical is pumped constantly (instead of being cycled together with water and pre-mix).

Figure 10:
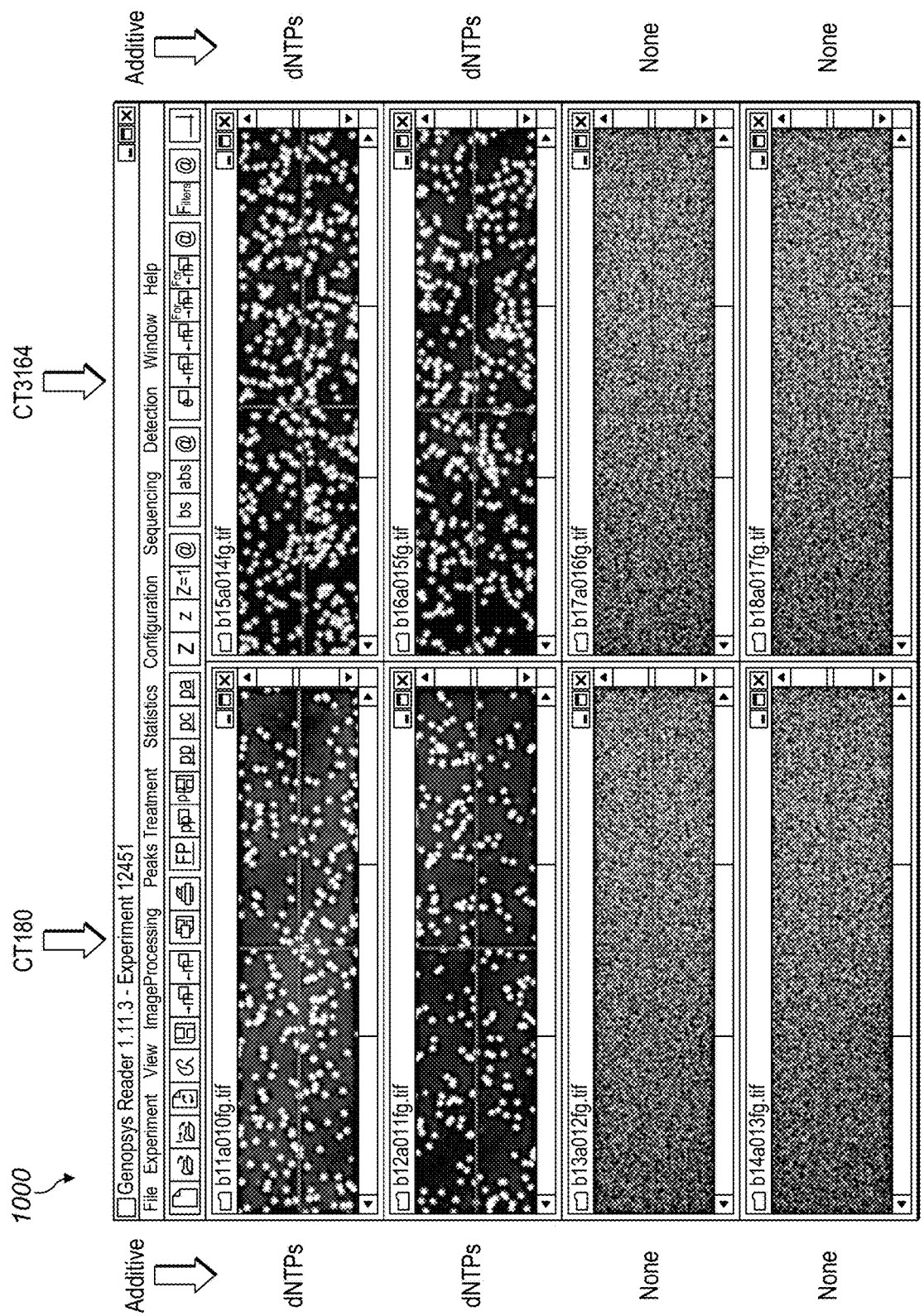
FIG. 10 shows panels of clusters stained with SYBR® Green generated by isothermal amplification using formamide with and without added dNTPs.

To determine whether the addition of dNTPs may rescue clonal amplification when a relatively large volume of formamide is used in an isothermal amplification process, amplification was performed using 120 µL of formamide with or without the addition of dNTPs. FIG. 10 shows panels of clusters 1000 generated by isothermal amplification using formamide with and without added dNTPs. In this example, two templates were used, CT180 (a GC-rich template) and CT3164 (an AT-rich template). The left-hand panels, from top to bottom, represent lanes 1 through 4 of the flow cell. The right-hand panels, from top to bottom, represent lanes 5 through 8 of the flow cell. Lanes 1 through 4 on the flow cell were seeded with 0.6 pM of CT180; lanes 5 through 8 on the flow cell were seeded with 0.6 pM of CT3164. After the first strand extension using Taq DNA polymerase, followed by NaOH denaturation, cluster amplification was performed using 26 isothermal amplification cycles of 120 µL of formamide (a relatively large volume compared to the standard 28 µL of formamide), followed by 28 µL of water, and 36 µL of standard Bst mix. Clusters were visualized by staining with SYBR® Green and imaged. A representative tile from each lane is shown in FIG. 9. The data show that while both the CT180 and CT3164 templates fail to be amplified in an isothermal amplification process using a relatively large volume of formamide, cluster amplification is rescued by the addition of dNTPs into the formamide solution.

FIG. 11 shows a data table 1100 of sequencing metrics for a sequencing run evaluating the "dNTPs" method and the "water" method. The dNTPs method includes the addition of dNTPs to both a first solution of formamide and a second solution of water. The water method replaces a second solution of pre-mix with water. In this experiment CT4008 (standard BCG library, GC rich genome; average insert size of 300 bp) was seeded at either low density (1.5 pM) or high density (7.5 pM). After standard first strand extension with Phusion DNA polymerase, clusters were amplified with 26 cycles of isothermal amplification using different conditions: No-premix=28 µL formamide and 64 µL Bst mix; pre-mix=28 µL formamide, 28 µL pre-mix, and 36 µL Bst mix; water method=28 µL formamide, 28 µL water, and 36 µL Bst mix; dNTPs method=28 µL formamide containing 200 µM each nucleotide, 28 µL water containing 200 µM each nucleotide, and 36 µL Bst mix. This run was analyzed with Pipeline 1.8. The flow cell was sequenced with 36 cycles of SBS using 95G chemistry on a Genome Analyzer IIx.

For the BCG genome, there was a significant increase in terms of clusters passing filter (see "% PF clusters" column data table 1100) for both the "water" and "dNTPs" methods compared to the no-premix and the standard amplification methods (labelled "pre-mix" in the Figure). The brightest clusters were obtained with the "dNTPs method" (compare lanes 6 and 8 with lanes 4 and 7).

Figure 12A:
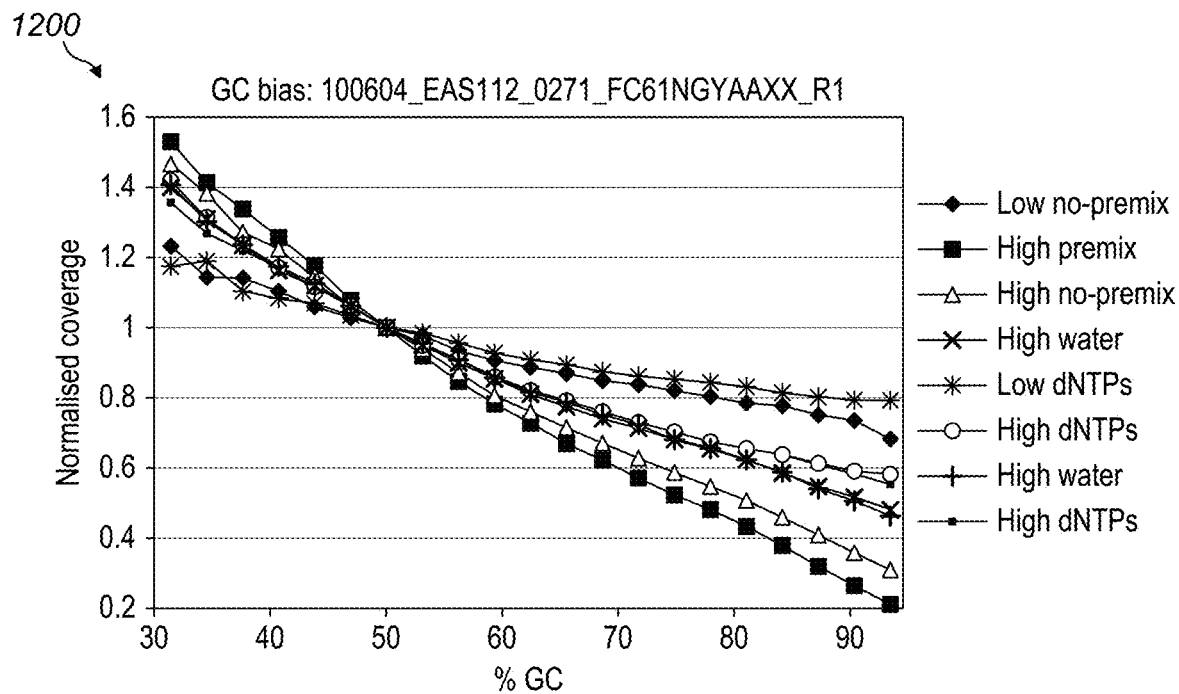
FIG. 12A and FIG. 12B show curves of GC bias and curves of GC bias normalized to low density lane 1, respectively, of the sequencing run described with reference to FIG. 11.
Figure 12B:
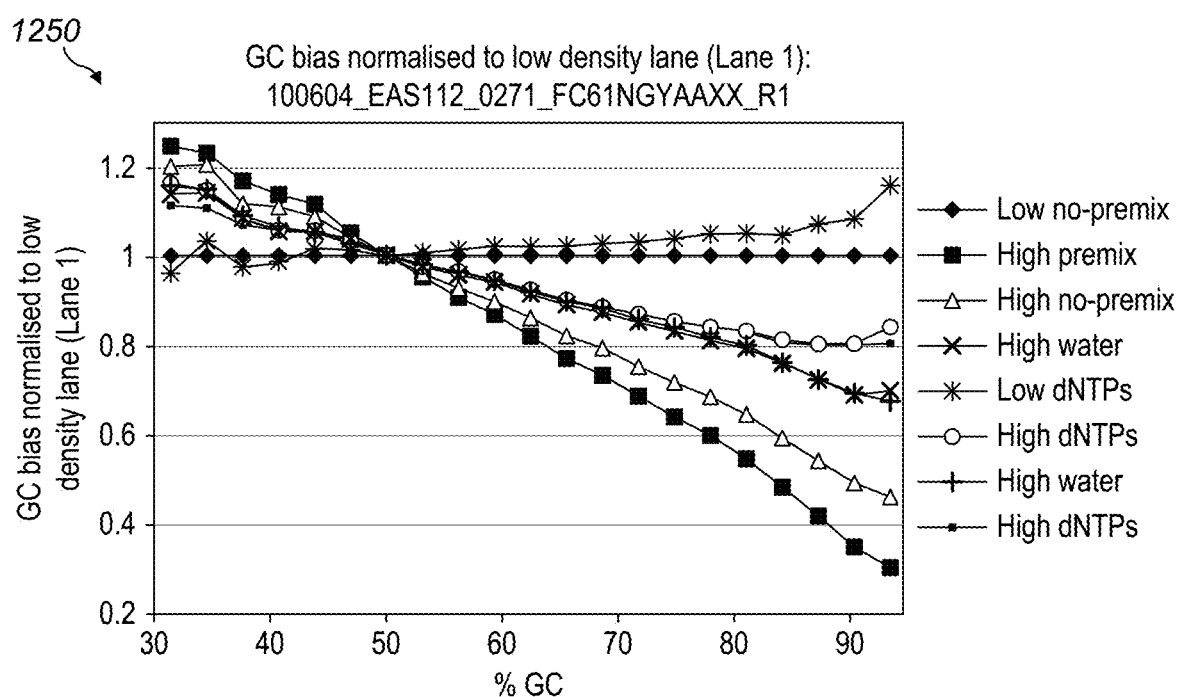

FIGS. 12A and 12B show curves 1200 of GC bias and curves 1250 of GC bias normalized to low density lane 1, respectively, of the sequencing run described with reference to FIG. 11.

Figure 13A:
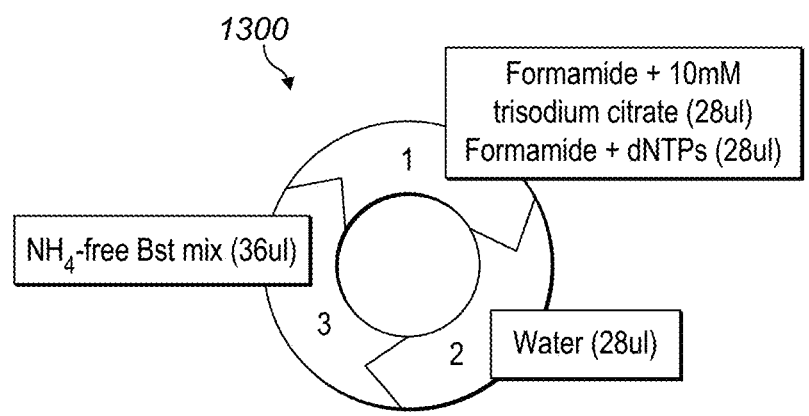
FIG. 13A shows a summary schematic diagram of bridge amplification solutions according to the methods of the invention.
Figure 13B:
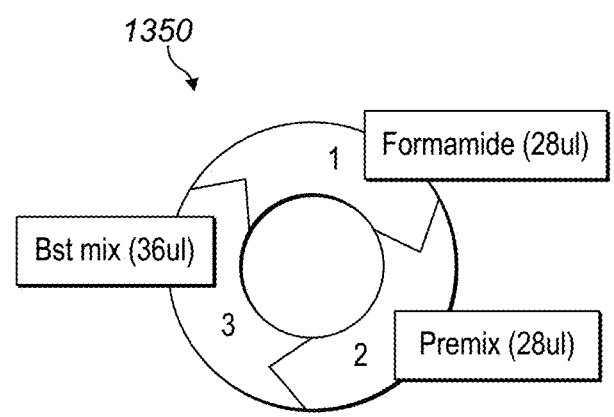
FIG. 13B shows a summary schematic diagram of bridge amplification solutions according to a standard method.
Figure 14:
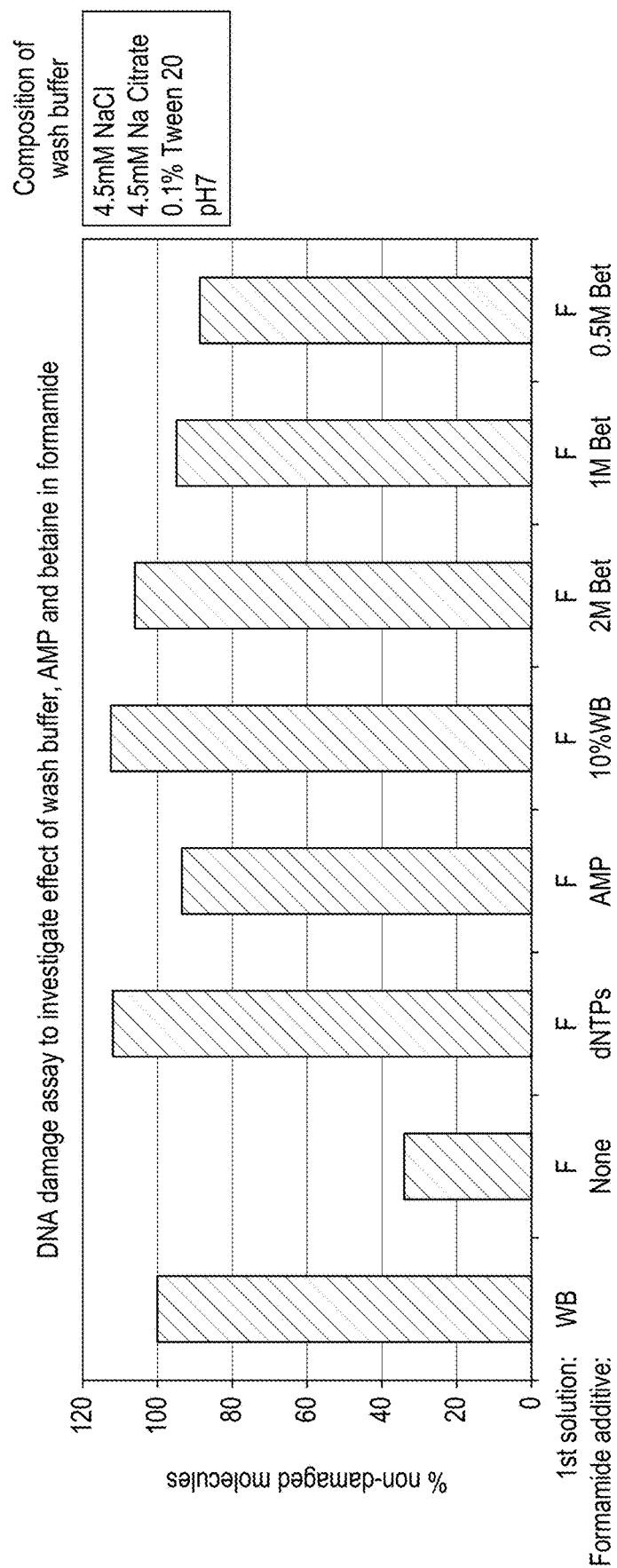
FIG. 14 shows the effect of various formamide additives on DNA damage by isothermal cluster amplification reagents (FC61WEBAAXX, exp 12374). CT180 was seeded at 1 pM. 1st strand extension was done using Taq DNA polymerase followed by NaOH denaturation. Single molecules were then treated with 26 cycles of "mock isothermal amplification (28 µl formamide, 28 µl H$_2$O, 36 µl premix with dNTPs. The control lane was treated with wash buffer for the entire duration). WB=wash buffer. dNTPs=200 µM of each nucleotide. AMP=adenosine monophosphate at 800 µM final concentration. 2M betaine in formamide=60% formamide containing betaine at final concentration of 2M and water. 1M betaine in formamide=80% formamide containing betaine at final concentration of 1M and water. 0.5M betaine in formamide=90% formamide containing betaine at final concentration of 0.5M and water.
Figure 15:
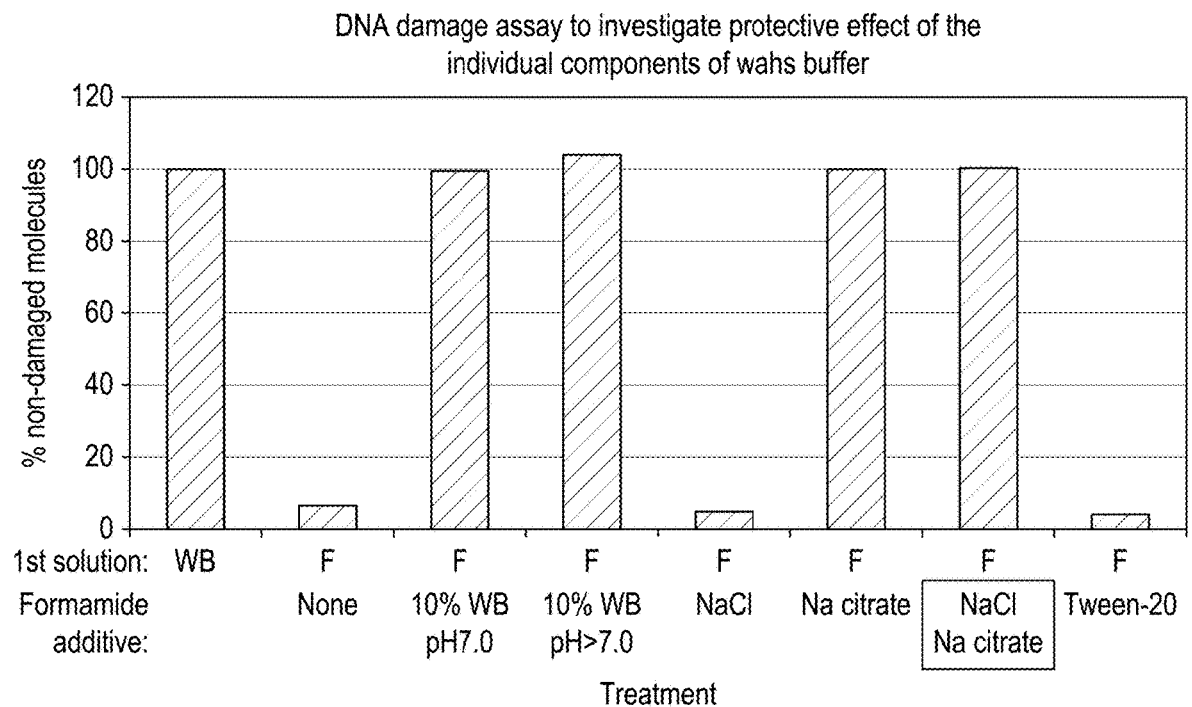
FIG. 15 depicts a protective effect against DNA damage of each individual component of wash buffer (FC62263AAXX exp 12402). CT180 was seeded at 0.6 pM. 1st strand extension was done using Taq DNA polymerase followed by NaOH denaturation. Single molecules were then treated with 26 cycles of "mock isothermal amplification (28 µl formamide with various additives, 28 µl H$_2$O, 36 µl premix with dNTPs.) Lane 1 acted as a control and was treated with wash buffer for the entire duration of the treatment. 2nd and 3rd solutions were 28 µl of H$_2$O and 36 µl of pre-mix/dNTPs respectively for all lanes except for lane 1 in which wash buffer was pumped instead. WB=wash buffer. dNTPs=200 µM of each nucleotide. Each additive was added to a concentration that is identical to that which would be reached when adding 10% of wash buffer (4.5 mM NaCl, 0.45 mM Na Citrate, 0.01% tween-20).
Figure 16:
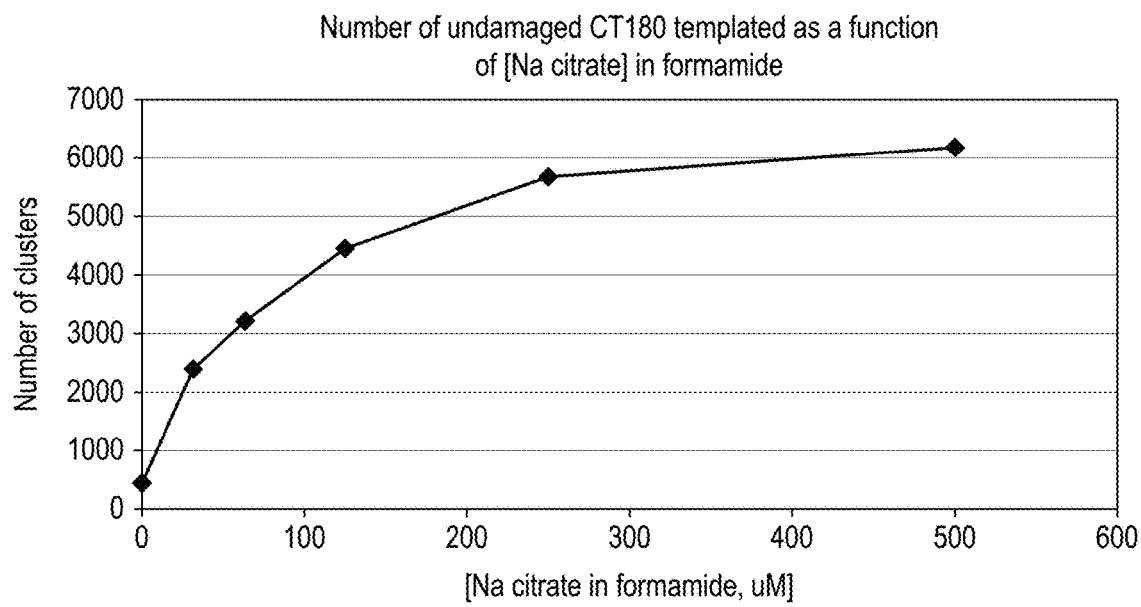
FIG. 16 depicts an effect of the concentration of sodium Citrate in formamide on DNA damage (FC62272AAXX, exp 12411). CT180 was seeded at 0.6 pM. 1st strand extension was done using Taq DNA polymerase followed by NaOH denaturation. Single molecules were then treated with 26 cycles of "mock isothermal amplification (28 µl formamide, 28 µl H$_2$O and 36 µl premix with dNTPs). One lane was used as a control and was treated by pumping wash buffer for the entire duration of the treatment. At the end of the treatment, cluster amplification was performed using 26 cycles of isothermal amplification (28 µl formamide+64 µl Bst mix). Clusters were then stained with sybr green and three tiles per lane were imaged using a microscope and a camera. Clusters numbers were determined using a software called Firecrest.
Figure 18B:
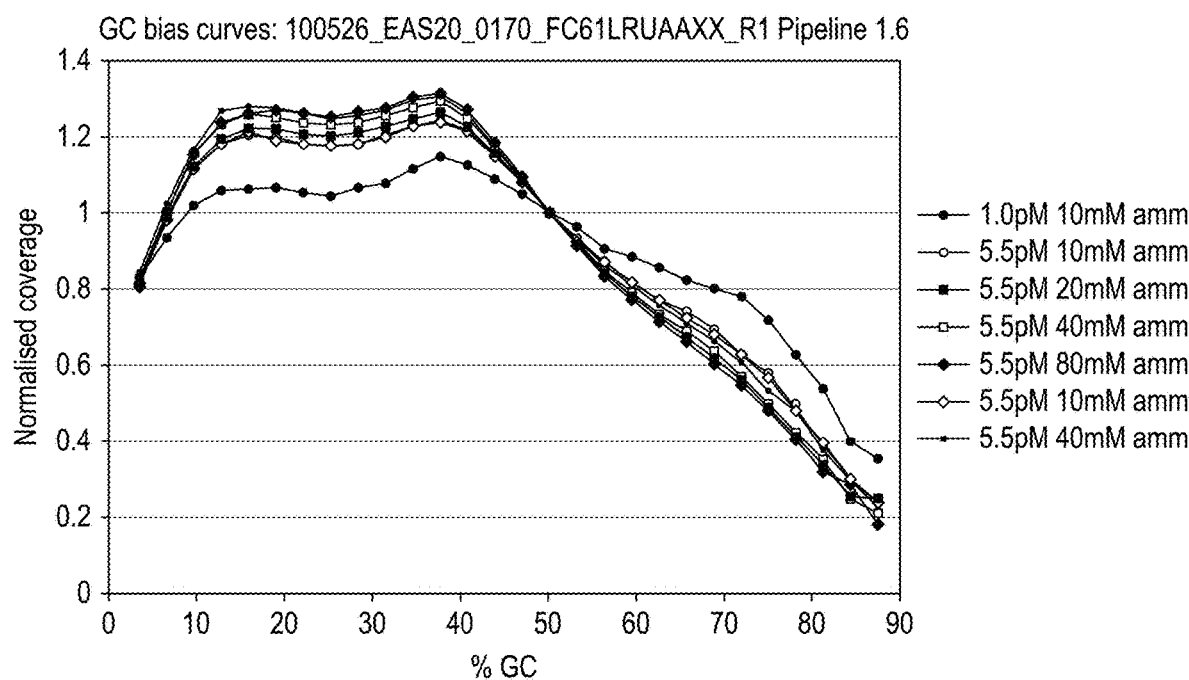
Figure 18C:
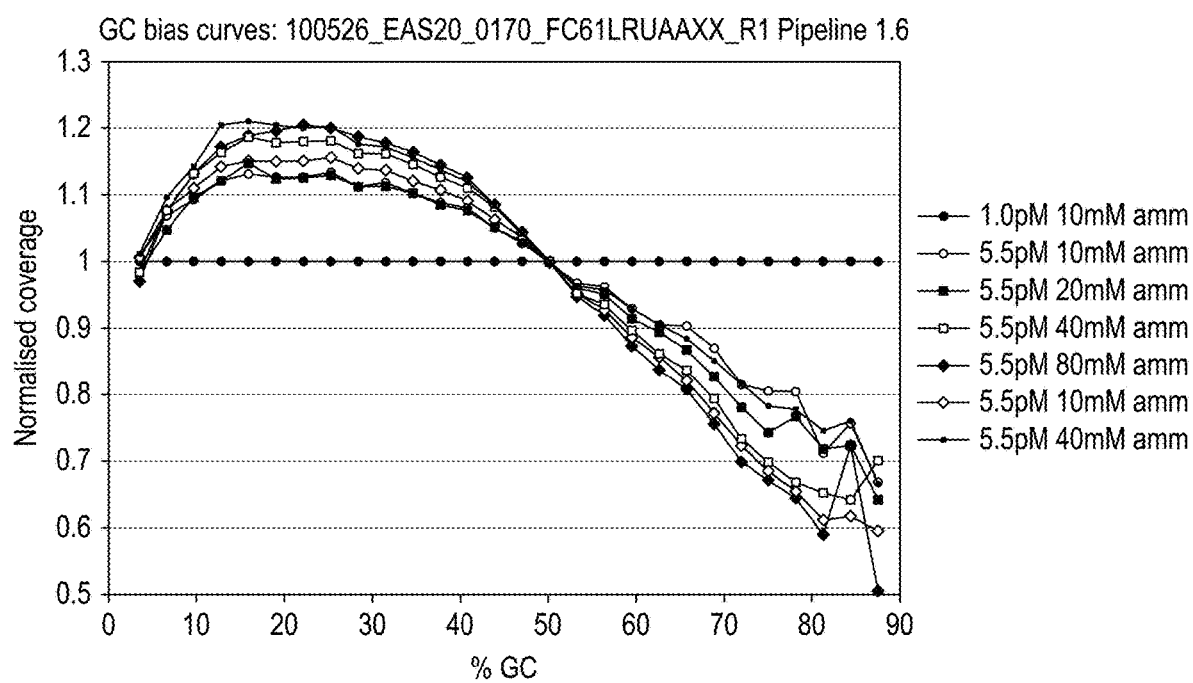
Figure 19C:
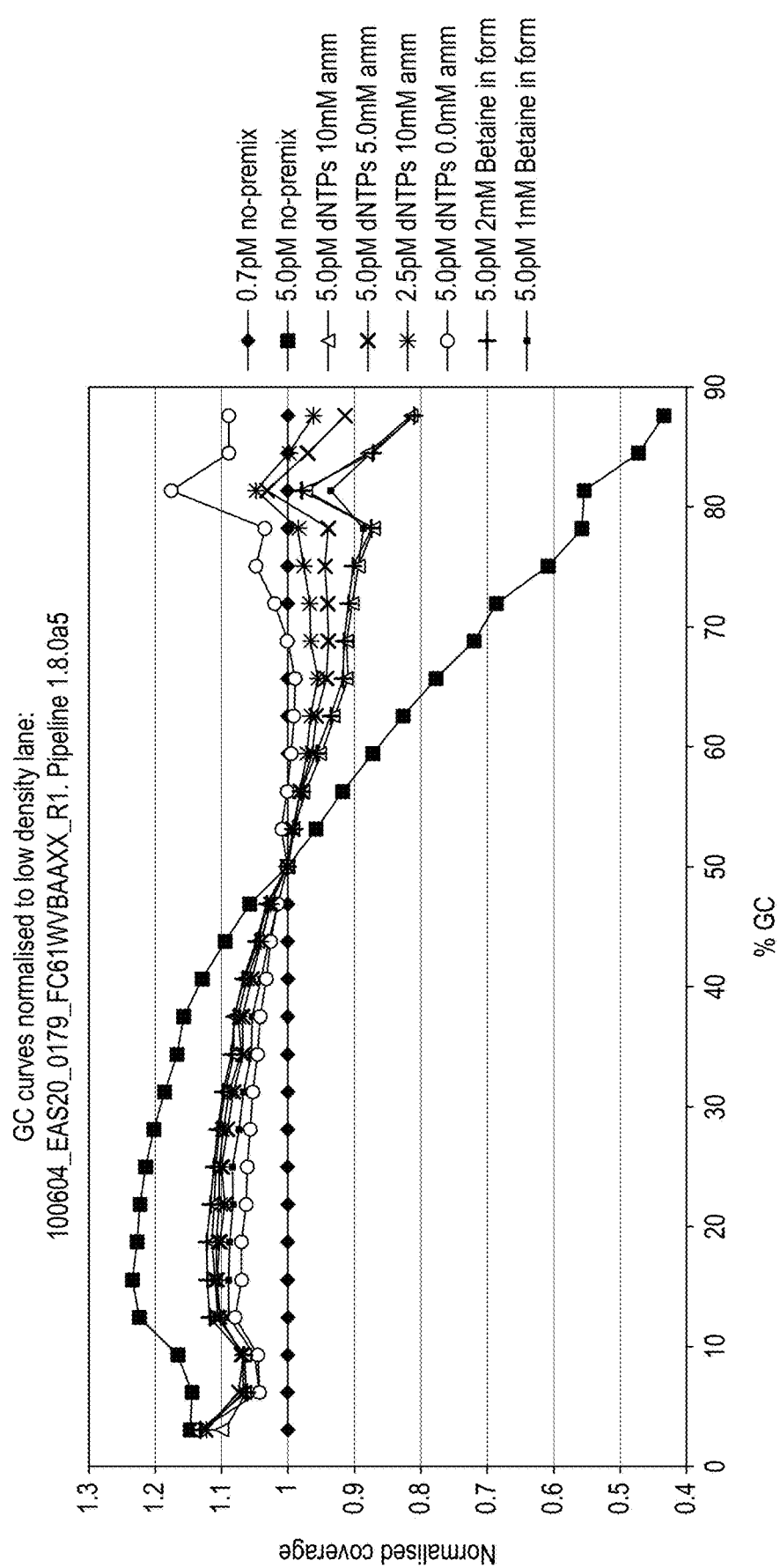
Figure 20C:
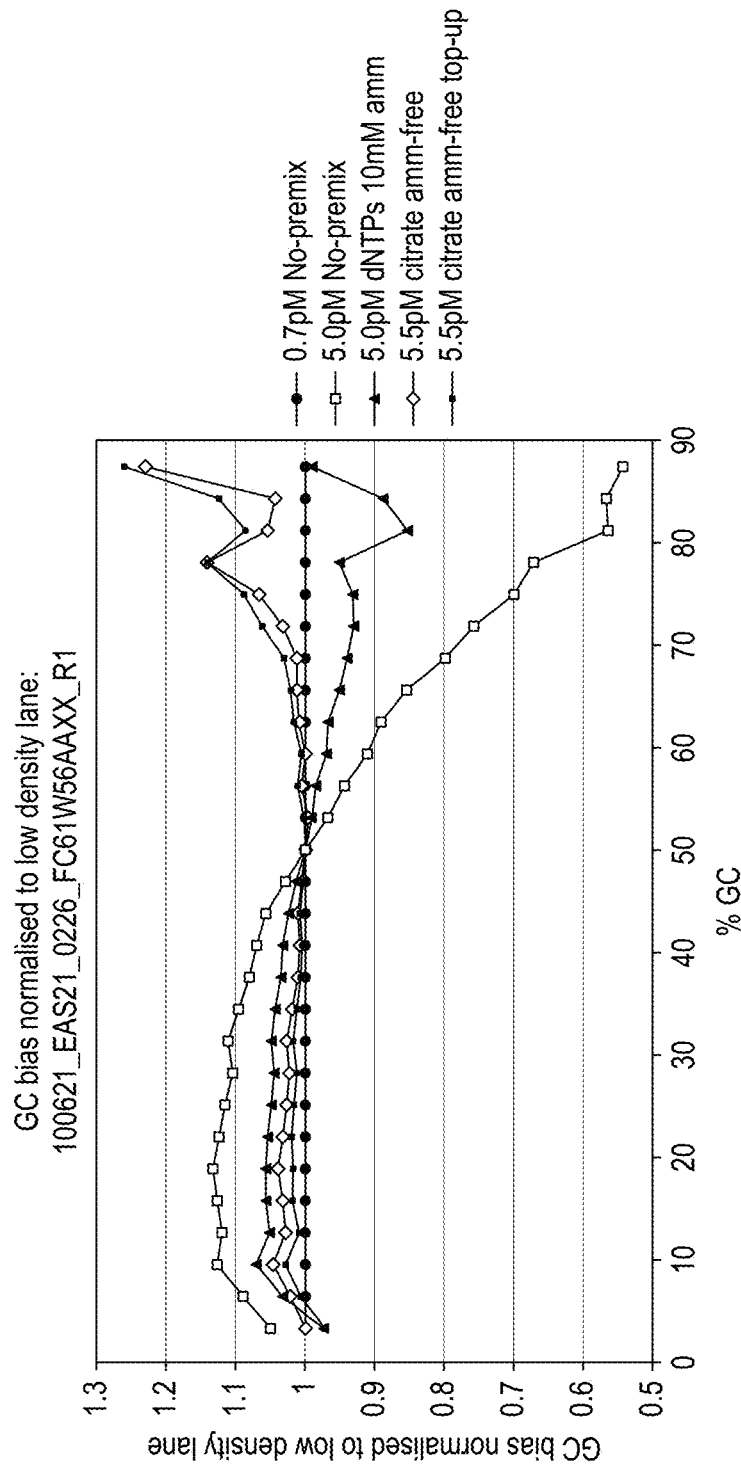
Figure 20D:
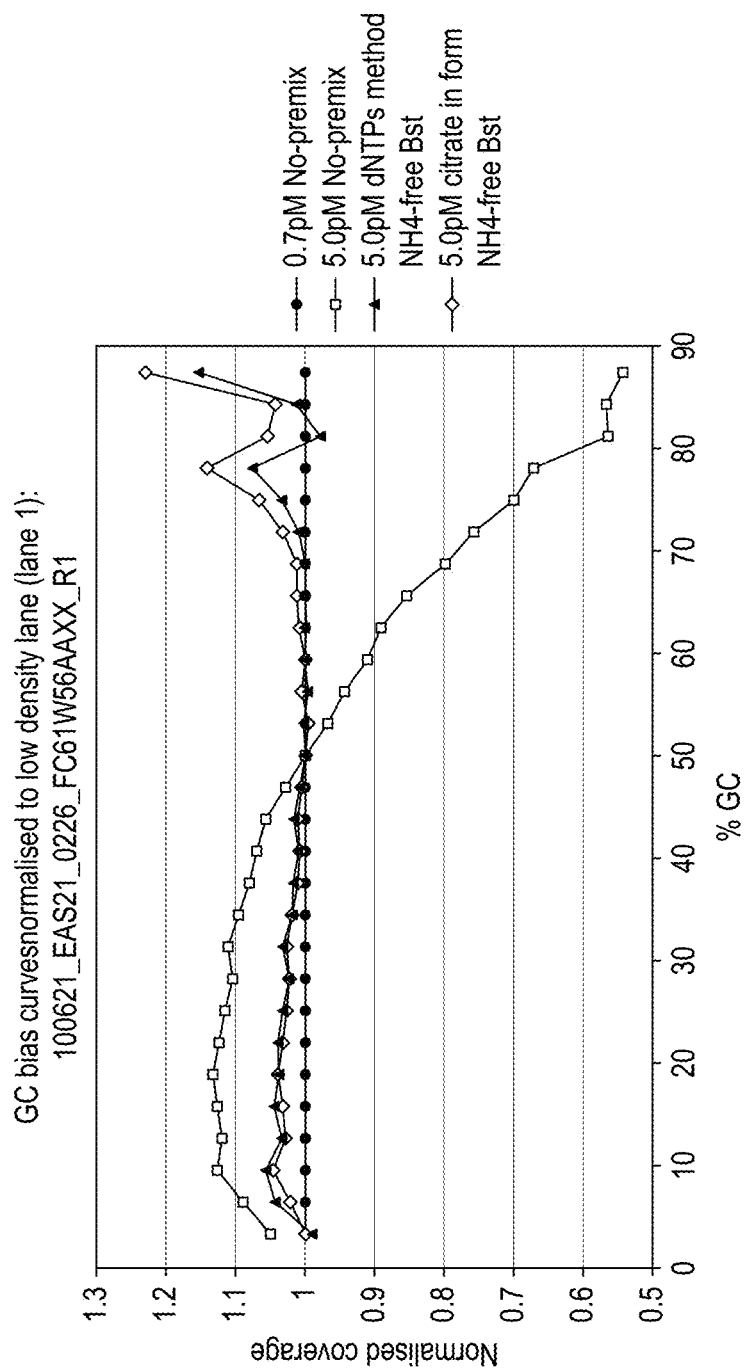
Figure 21C:
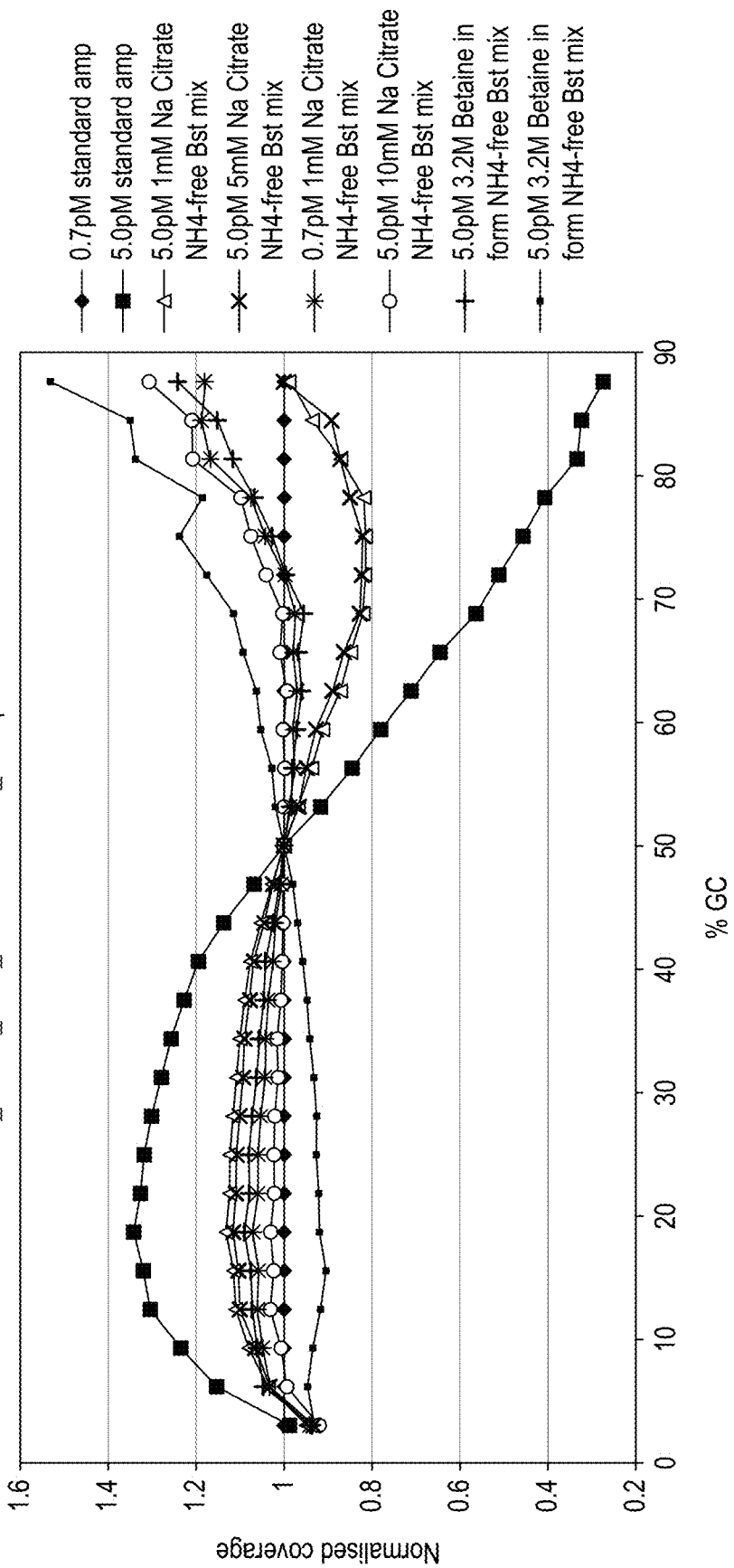

FIG. 13A shows a summary schematic diagram 1300 of bridge amplification solutions according to the methods of the invention, while FIG. 13B shows a summary schematic diagram 1350 of bridge amplification solutions according to a standard method. In one embodiment, trisodium citrate is used in a final concentration of 1 mM in formamide.

In another aspect of the present invention, solid phase amplification can be performed efficiently in a flow cell since it is a feature of the invention that the primers, template and amplified (extension) products may all remain immobilized to the solid support during the amplification. Accordingly, an apparatus is provided that can allow immobilized nucleic acids to be isothermally amplified. An apparatus may also include a source of reactants and detecting means for detecting a signal that may be generated once one or more reactants have been applied to the immobilized nucleic acid molecules. An apparatus may also be provided with a surface comprising immobilized nucleic acid molecules in the form of colonies.

In one embodiment, an apparatus is provided comprising one or more of the following:
a) at least one inlet
b) means for immobilizing primers on a surface (although this is not needed if immobilized primers are already provided);
c) means for substantially isothermal amplification of nucleic acids (e.g. denaturing solution, hybridizing solution, extension solution, wash solution(s));
d) at least one outlet; and
e) control means for coordinating the different steps required for the method of the present invention.

In other embodiments, as a volume of a particular suitable solution in contact with a solid support is removed, it is replaced with a similar volume of either the same or a different solution. Thus, solutions applied to a flow cell through an inlet can be removed via an outlet by a process of solution exchange.

Desirably, a means for detecting a signal has sufficient resolution to enable it to distinguish between and among signals generated from different colonies. Instruments that are useful for detecting a fluorescent signal are described, for example, in WO 2007/123744, US 2010/0111768 and U.S. Pat. No. 7,329,860, the contents of which are incorporated by reference herein in their entireties.

Apparatuses of the present invention are preferably provided in automated form so that once they are activated, individual process steps can be repeated automatically.

Concluding Remarks

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

What is claimed is:

1. A system for reducing density-dependent GC bias in a bridge amplification of double-stranded DNA templates on a surface, the system comprising:
an apparatus having at least one inlet for applying solution to the surface, and at least one outlet for removing solution from the surface, wherein the at least one inlet and the at least one outlet allow a denaturation solution and an extension solution to be sequentially passed over the surface, wherein:
the surface comprises a plurality of primers and a plurality of extended primers, each primer and extended primer bound on to the surface, wherein the plurality of primers are capable of annealing to the plurality of extended primers;
the denaturation solution is in contact with the outlet, wherein the denaturation solution comprises formamide and an additive comprising at least one type of deoxynucleotide triphosphate (dNTP); and
the extension solution is in contact with the inlet, wherein the extension solution comprises a polymerase and a mixture of different nucleotides.

2. The system of claim 1, wherein the apparatus comprises means for immobilizing primers on a surface.

3. The system of claim 1, wherein the plurality of extended primers are clustered on the surface.

4. The system of claim 1, wherein the at least one type of dNTP in the denaturation solution is a mixture of four different types of dNTP, each of which is present at a concentration of 200 μM.

5. The system of claim 1, wherein the concentration of a single type of dNTP in the at least one type of dNTP is 200 μM.

6. The system of claim 1, wherein the denaturation solution further comprises betaine or a chelating agent.

7. The system of claim 6, wherein the concentration of the betaine in the denaturation solution is greater than or equal to 0.5 M and less than or equal to 2 M.

8. The system of claim 1, wherein the denaturation solution lacks magnesium cations.

9. The system of claim 1, wherein the extension solution lacks ammonium cations.

10. The system of claim 1, wherein the extension solution further comprises a component selected from the group consisting of betaine and DMSO.

11. The system of claim 1, further comprising a pre-mix solution in contact with the surface, wherein the pre-mix solution comprises at least one type of dNTP.

12. The system of claim 11, wherein the pre-mix solution further comprises a component selected from the group consisting of betaine and DMSO.

13. The system of claim 1, wherein the surface is adapted to maintain a temperature suitable for isothermal amplification of nucleic acids on the surface.

14. The system of claim 1, wherein a flow cell comprises the surface.

15. The system of claim 1, wherein a bead comprises the surface.

16. The system of claim 1, wherein the plurality of primers and the plurality of extended primers comprise DNA.

* * * * *